US008535898B2

(12) United States Patent
Qin et al.

(10) Patent No.: US 8,535,898 B2
(45) Date of Patent: Sep. 17, 2013

(54) THROMBIN SUBSTRATE AND ASSAY FOR DETERMINING THE LEVEL OF BIOACTIVE THROMBIN IN A SAMPLE

(75) Inventors: Qiu-Ping Qin, Turku (FI); Harri Takalo, Turku (FI); Allan Milton Byrnard, Ishoj (DK); Kirsten Marie Jakobsen, Copenhagen (DK)

(73) Assignee: Radiometer Medical APS, Bronshoj (DK)

( * ) Notice: Subject to any disclaimer, the term of this patent is extended or adjusted under 35 U.S.C. 154(b) by 816 days.

(21) Appl. No.: 12/503,602

(22) Filed: Jul. 15, 2009

(65) Prior Publication Data
US 2010/0184106 A1 Jul. 22, 2010

(30) Foreign Application Priority Data

Jul. 16, 2008 (DK) ................................. 2008 01004

(51) Int. Cl.
*A61K 38/06* (2006.01)
*A61K 38/07* (2006.01)
*C12Q 1/56* (2006.01)
*C07K 14/745* (2006.01)

(52) U.S. Cl.
USPC .......... 435/13; 514/14.7; 514/21.9; 424/1.69; 530/330; 530/331

(58) Field of Classification Search
None
See application file for complete search history.

(56) References Cited

U.S. PATENT DOCUMENTS

| 4,061,625 | A | * | 12/1977 | Af Ekenstam et al. | ....... | 530/331 |
|---|---|---|---|---|---|---|
| 4,670,572 | A | | 6/1987 | Hinshaw et al. | | |
| 4,761,481 | A | | 8/1988 | Hale et al. | | |
| 4,772,563 | A | | 9/1988 | Evangelista et al. | | |
| 4,794,191 | A | | 12/1988 | Hinshaw et al. | | |
| 4,801,722 | A | | 1/1989 | Hinshaw et al. | | |
| 4,859,777 | A | | 8/1989 | Toner | | |
| 4,920,195 | A | | 4/1990 | Kankare et al. | | |
| 4,927,923 | A | | 5/1990 | Mathis et al. | | |
| 5,032,677 | A | | 7/1991 | Hale et al. | | |
| 5,055,578 | A | | 10/1991 | Hale et al. | | |
| 5,202,423 | A | | 4/1993 | Kankare et al. | | |
| 5,216,134 | A | | 6/1993 | Mukkala et al. | | |
| 5,324,825 | A | | 6/1994 | Kankare et al. | | |
| 5,571,897 | A | | 11/1996 | Takalo et al. | | |
| 5,859,215 | A | | 1/1999 | Rodriguez-Ubis et al. | | |
| 7,018,851 | B2 | | 3/2006 | Takalo et al. | | |
| 2002/0192719 | A1 | | 12/2002 | Nikiforov et al. | | |
| 2003/0170746 | A1 | | 9/2003 | Huang et al. | | |
| 2005/0181393 | A1 | | 8/2005 | Hovinen et al. | | |

FOREIGN PATENT DOCUMENTS

| EP | 0493745 | 7/1992 |
|---|---|---|
| EP | 0369000 | 4/1999 |
| EP | 1 889 919 A1 | 2/2008 |
| FI | EP 1 447 666 A2 * | 8/2004 |
| FI | EP-1447662 * | 8/2004 |
| GB | 2384857 | 8/2003 |
| IT | 1235668 | 9/1992 |
| JP | 2003-245096 A | 9/2003 |
| WO | WO 92/14841 | 9/1992 |
| WO | WO 93/05049 | 3/1993 |
| WO | WO 2005/021538 | 3/2005 |
| WO | WO 2006/123789 A1 | 11/2006 |
| WO | WO 2008/020113 | 2/2008 |

OTHER PUBLICATIONS

Qin, 2001, Clin. Chem. Lab. Med., 39, PO-E026 (Poster).*
Grant, 2004, Sensor Letters, 2, 164-170.*
Biosclair et al. "Development of a ubiquitin transfer assay for high throughput screening by fluorescence resonance energy transfer" Journal of Biomolecular Screening 5(5): 319-328 (2000).
Grant et al. "A novel sensing technique to detect thrombin" Sensor Letters 2(3-4): 164-170 (2004).
Jean et al. "Detection of endopeptidase activity and analysis of cleavage specificity using a radiometric solid-phase enzymatic assay" Anal Biochem. 194(2): 399-406 (1991).
Scully et al "Methods for semi micro or automated determination of thrombin, antithrombin, and heparin cofactor using the substrate, H-d-Phe-Pip-Arg-p-nitroanilide • 2HC1" Clinica Chimica Acta 79(3): 595-602 (1977).
Taki et al. "A chiral Eu3+—thienoyltrifluoroacetone complex on an avidin tetramer: luminescence and CD studies on the supramolecular protein—metal chelate complex" Chemical Communications 13: 1199-1200 (2000).
International Search Report and Written Opinion issued in PCT Application No. PCT/DK2009/000169 (Jan. 15, 2010).
Bush et al., "Solid-phase time-resolved fluorescence detection of human immunodeficiency virus polymerase chain reaction amplification products", Anal. Biochem., 202(1):146-151 (1992).
Hemmila et al., "Di- and tetracarboxylate derivatives of pyridines, bipyridines and terpyridines as luminogenic reagents for time-resolved fluorometric determination of terbium and dysprosium", J. Biochem. Biophys. Methods, 26(4):283-290 (1993).
Latva et al., "Correlation between the lowest triplet state energy level of the ligand and lanthanide(III) luminescence quantum yield", J. Luminescence, 75(2): 149-169 (1997).
Sato et al., "Energy-transfer luminescence of lanthanide ions encapsulated in sensitizer-modified calix[4]arenes", J. Chem. Soc. Perkin Trans., 2: 621-624 (1993).
Selvin et al., "Luminescence Resonance Energy Transfer", J. Am. Chem. Soc., 116 (13): 6029-6030 (1994).
Steemers et al., "New Sensitizer-Modified Calix[4]arenes Enabling Near-UV Excitation of Complexed Luminescent Lanthanide Ions", J. Am. Chem. Soc., 117 (37): 9408-9414 (1995).

(Continued)

*Primary Examiner* — Satyanarayana R Gudibande
(74) *Attorney, Agent, or Firm* — Morgan Lewis Bockius LLP

(57) ABSTRACT

Substrates for thrombin and assays for determining the level of bioactive thrombin in a sample are disclosed, wherein the substrate has the general formula: A-X—Z-A' wherein one of either A or A' comprises a luminescent chelate and the other one of A or A' comprises a first partner of a binding pair, X forms a tri- or tetra-peptide, and Z comprises a linker.

13 Claims, 6 Drawing Sheets

(56) References Cited

OTHER PUBLICATIONS

Takalo et al., "Synthesis and luminescence of novel $Eu^{III}$ complexing agents and labels with 4-(phenylethynyl)pyridine subunits", Helvetica Chimica Acta, 79:789-802 (1996).
Takalo et al., "Synthesis of europium(III) chelates suitable for labeling of bioactive molecules", Bioconjug. Chem., 5(3):278-282 (1994).
Von Lode et al., "A europium chelate for quantitative point-of-care immunoassays using direct surface measurement", Anal. Chem., 75(13):3193-3201 (2003).
D. Wild, "The immunoassay handbook", Nature publishing group, 2001, pp. 167-168.
Basak et al. "Radiolabeled biotinyl peptides as useful reagents for the study of proteolytic enzymes" Analytical Biochemistry 209(2): 306-314 (1993).

* cited by examiner

THROMBIN SUBSTRATE AND ASSAY FOR DETERMINING THE LEVEL OF BIOACTIVE THROMBIN IN A SAMPLE

CROSS-REFERENCE TO RELATED APPLICATIONS

This application claims priority from Danish Patent Application No. PA 2008 01004, filed on Jul. 16, 2008, which is incorporated by reference in its entirety.

FIELD OF THE INVENTION

The present invention relates to novel substrates for thrombin and assays for determining the level of bioactive thrombin in a sample.

BACKGROUND OF THE INVENTION

Thrombin is produced by the enzymatic cleavage of two sites on prothrombin by activated Factor X (Xa).

Thrombin converts fibrinogen to an active form that assembles into fibrin. Thrombin also activates Factor XI, Factor V and Factor VIII. This positive feedback accelerates the production of thrombin.

Factor XIII is also activated by thrombin. Factor XIIIa is a transglutaminase that catalyses the formation of covalent bonds between lysine and glutamine residues in fibrin. The covalent bonds increase the stability of the fibrin clot.

In addition to its activity in the coagulation cascade, thrombin also promotes platelet activation, via activation of protease-activated receptors on the platelet.

In clinical practice the measurement of prothrombin time (PT), i.e., the time it takes for blood to clot, in terms of activated partial thromboplastin time (APTT) and activated clotting time (ACT), is widely used for screening for defects of coagulation pathways and for monitoring anticoagulant therapy.

In order to standardize the results of blood coagulation tests, the concept of International Normalized Ratio (INR) has been devised. Each manufacturer of tissue factors gives an ISI (International Sensitivity Index) for any tissue factor they make. The ISI value indicates the comparison between a particular batch of tissue factor and an internationally standardized sample. As depicted below, INR is the ratio of a patient's prothrombin time to a control sample's prothrombin time, raised to the power of the ISI value for the thromboplastin reagent used.

$$INR = (PT_{test}/PT_{normal})^{ISI}$$

There are two kinds of assays available for the measurement of PT. One kind of assay is coagulometric, which is based on the endpoint of clot formation from fibrinogen to fibrin conversion. The results of the assays are, however, variable, and particularly affected by interference with the fibrinogen/fibrin conversion in patients. Another kind of assay is non-coagulometric and is based on the use of synthetic substrates suitable for thrombin cleavage. The results of the latter assays are less variable and not affected by the fibrinogen level.

U.S. Pat. No. 4,061,625 discloses chromogenic thrombin substrates of the formula D-Phe-cyclic imino acid-Arg-pNA wherein the cyclic imino acid is selected from among 2-azetidine carboxylic acid, proline, 2-piperidine carboxylic acid, and pNA is p-nitroanilide. These substrates are described as suitable for a quantitative determination of thrombin or for a study of reactions in which thrombin is formed, inhibited or consumed, or for determination of factors which exert an influence or take part in such reactions e.g., for determination of anti-thrombin, prothrombin and heparin.

When chromogenic substrates are used, the reaction is detected at approximately 405 nm. At this wavelength, whole blood can not be analysed, due to the absorption from the whole blood in its self. Chromogenic substrates are therefore not suitable when the used sample type is whole blood.

Time-resolved luminescence spectroscopy using chelates such as lanthanide chelates has for several years been applied in immunoassays and DNA hybridization assays. Due to the absorption properties of whole blood, this chelate detection technology is suitable when the sample is whole blood, compared to the chromogenic substrates, because it is possible with this technology to measure absorbance at 615 nm, at which wavelength, whole blood absorption is low.

Such chelates are described in U.S. Pat. No. 7,018,851 B1 which discloses improved fluorescent lanthanide chelates which are suitable for time-resolved fluorometric (TRF) applications. The chelates are used in specific bioaffinity based binding assays such as immunoassays.

TRF is a suitable detection technology for assays requiring high sensitivity and wide dynamic range. In immunoassay techniques using conventional fluorescence detection, high non-specific background caused by light scattering, e.g., from the biological components of the sample is a severe limitation to the sensitivity of the assay.

The fluorescent lanthanide chelates have traditionally been used in immunoassays where the detection principle is based on the capture of such chelates and detection thereof. In contrast they have not been used in enzyme assays, where the detection principle is based on cleavage of the chelate substrate and detection of the captured (not cleaved) substrate remaining in the assay.

The key feature of such a system is the provision of a substrate which is on the one hand stable and on the other hand specifically cleavable by thrombin.

Therefore, there exists a need for an enzyme substrate which is specifically cleavable by thrombin and which comprises an intrinsic stable luminescent component having a long lifetime, thus facilitating detection in whole blood and resulting in less interference.

Furthermore there exists a need for an assay which is fast, easy to perform, subject to low variability, easily automated, and of low cost.

Surprisingly it has been found that by combining, via a certain linker, a peptide which is specifically cleavable by thrombin, with a luminescent chelate, a stable substrate with a long lifetime, which can be used when the sample type is whole blood, is provided.

SUMMARY OF THE INVENTION

In a first aspect, the present invention is a substrate for thrombin having the formula:

A-X—Z-A' wherein
one of either A or A' comprises a luminescent chelate, and
the other one of A or A' comprises a first partner of a binding pair, optionally including a spacer, and connected via a peptide bond to the remaining part of the substrate,
X forms a tri- or tetra-peptide selected from among X'-Phe-Aze-Arg, X'-Phe-Pip-Arg, and X'-Phe-Pro-Arg, wherein X' is absent or selected among Lys, Ahx, Ile, and Val, Z is NH—R—Z', wherein
R is selected from the group consisting of $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, $C_{1-6}$alkylenoxy-carbonyl, $C_{1-6}$alkylene-arylene, $C_{1-6}$alkylenoxy-arylene, $C_{1-6}$alkylene-NH, $C_{1-6}$alkylenoxy-NH, $C_{1-6}$alkylene-NHCO, $C_{1-6}$alkylenoxy-NHCO, $C_{1-6}$alkylene-CONH, $C_{1-6}$alkylenoxy-CONH, $C_{1-6}$alkylene-COS, $C_{1-6}$alkylenoxy-COS, $C_{1-6}$alkylene-CONH—$C_{1-6}$alkylene-arylene, arylene, arylene-$C_{1-6}$alkylene, arylene-$C_{1-6}$alkylenoxy, $R^1{}_a$-arylene-(NHCO—$R^2)_b$, $R^3{}_c$-arylene-(CONH—$R^4)_d$, $(R^5$—CONH$)_e$-arylene-$R^6{}_f$, and $(R^7$—NHCO$)_g$-arylene-$R^8{}_h$,
wherein each $R^1$, $R^2$, $R^3$, $R^4$, $R^5$, $R^6$, $R^7$, and $R^8$ at each occurrence is independently selected from among $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, arylene and arylene-$C_{1-6}$alkylene, and wherein each of a, b, c, d, e, f, g, and h is independently selected from among the integers from 0 to 6,
wherein the arylene is phenylene, biphenylene or naphthylene, which phenylene, biphenylene or naphthylene is optionally mono-, di- or tri-substituted by one or more substituents selected from among halogen, OH, SH, CN, $NO_2$, $C_{1-6}$alkyl, $C_{1-6}$alkoxy, and $C_{1-6}$alkoxycarbonyl,
Z' comprises one of N, S, and carbonyl, wherein,
when Z' comprises N, Z' is selected from among thiourea (—NH—CS—NH—), aminoacetamide (—NH—CO—$CH_2$—NH—), amide (—NH—CO—), methylamide (—$NCH_3$—CO—) and substituted-triazine-diamine (—NH—($R^9C_3N_3$)—NH—),
when Z' comprises S, Z' is selected from among thioether (—S—), thioacetamide (—S—$CH_2$—CO—NH—), disulfide (—S—S—), (—S—CO—$CH_2$—NH—) and (—S—($R^9C_3N_3$)—NH—) or
when Z' comprises carbonyl, Z' is selected from among an amide (—CO—NH—, —CO—$NCH_3$—) and an ester (—CO—O—),
wherein $R^9$ is selected from the group consisting of hydrogen, halogen, $C_{1-6}$alkyl, $C_{1-6}$thioalkyl, $C_{1-6}$alkoxy, $C_{1-6}$thioalkoxy, aryloxy, and amino, which alkyl, thioalkyl, alkoxy, thioalkoxy or aryloxy group is optionally mono-, di- or tri-substituted and which amino group is optionally mono- or di-substituted by one or more substituents selected from among halogen, OH, SH, CN, $NO_2$, $C_{1-6}$alkyl, $C_{1-6}$alkoxy, and $C_{1-6}$alkoxycarbonyl.

Another aspect of the invention is a one-step assay method for determining the level of bioactive thrombin in a test sample comprising the steps:
a) combining, sequentially, simultaneously or substantially simultaneously, a substrate according to claim 1, an activator and said test sample;
b) incubating the resulting reaction mixture to release thrombin-cleaved, chelate-containing substrate fragments and immobilising the binding partner-containing substrate fragment and non-thrombin-cleaved intact substrate on an immobilisation matrix;
c) washing off non-immobilised, thrombin-cleaved chelate-containing substrate fragment and non-immobilised, non-thrombin-cleaved substrate, if present;
d) measuring the level of luminescent emission from immobilized intact substrate; and
e) calculating thrombin activity from the reduction of intensity of luminescent emission compared to a thrombin-free standard sample.

Another aspect of the invention is a two-step assay method for determining the level of bioactive thrombin in a test sample comprising the steps:
a) adding said sample and an activator to a substrate according to claim 1 in liquid phase,
b) incubating the resulting reaction mixture to release thrombin-cleaved, chelate-containing substrate fragment,
c) adding the reaction mixture to an immobilisation matrix,
d) washing off non-immobilised, thrombin-cleaved chelate-containing substrate fragment and non-immobilised, non-thrombin-cleaved substrate, if present,
e) measuring the level of luminescent emission from immobilised intact substrate, and
f) calculating thrombin activity from the reduction of intensity of luminescent emission compared to a thrombin-free standard sample.

Another aspect of the invention is a test kit for determining the level of bioactive thrombin in a sample comprising
a) a luminescent substrate according to claim 1, and
b) a solid immobilisation matrix.

Another aspect of the invention is a substrate for an enzyme having the formula:

wherein
one of either A or A' comprises a luminescent chelate, and
the other one of A or A' comprises a first partner of a binding pair, optionally including a spacer, and connected via a peptide bond to the remaining part of the substrate,
X forms a tri- or tetra-peptide,
Z is NH—R—Z', wherein
R is selected from the group consisting of $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, $C_{1-6}$alkylenoxy-carbonyl, $C_{1-6}$alkylene-arylene, $C_{1-6}$alkylenoxy-arylene, $C_{1-6}$alkylene-NH, $C_{1-6}$alkylenoxy-NH, $C_{1-6}$alkylene-NHCO, $C_{1-6}$alkylenoxy-NHCO, $C_{1-6}$alkylene-CONH, $C_{1-6}$alkylenoxy-CONH, $C_{1-6}$alkylene-COS, $C_{1-6}$alkylenoxy-COS, $C_{1-6}$alkylene-CONH—$C_{1-6}$alkylene-arylene, arylene, arylene-$C_{1-6}$alkylene, arylene-$C_{1-6}$alkylenoxy, $R^1{}_a$arylene-(NHCO—$R^2)_b$, $R^3{}_c$-arylene-(CONH—$R^4)_d$, $(R^5$—CONH$)_e$-arylene-$R^6{}_f$, and $(R^7$—NHCO$)_g$-arylene-$R^8{}_h$,
wherein each $R^1$, $R^2$, $R^3$, $R^4$, $R^5$, $R^6$, $R^7$, and $R^8$ at each occurrence is independently selected from among $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, arylene and arylene-$C_{1-6}$alkylene, and each of a, b, c, d, e, f, g, and h is independently selected from among the integers from 0 to 6,
wherein the arylene is phenylene, biphenylene or naphthylene, which phenylene, biphenylene or naphthylene is optionally mono-, di- or tri-substituted by one or more substituents selected from among halogen, OH, SH, CN, $NO_2$, $C_{1-6}$alkyl, $C_{1-6}$alkoxy, and $C_{1-6}$alkoxycarbonyl,
Z' comprises one of N, S, and carbonyl, wherein,
when Z' comprises N, Z' is selected from among thiourea (—NH—CS—NH—), aminoacetamide (—NH—CO—$CH_2$—NH—), amide (—NH—CO—), methylamide (—$NCH_3$—CO—) and substituted-triazine-diamine (—NH—($R^9C_3N_3$)—NH—),
when Z' comprises S, Z' is selected from among thioether (—S—), thioacetamide (—S—$CH_2$—CO—NH—), disulfide (—S—S—), (—S—CO—$CH_2$—NH—) and (—S—($R^9C_3N_3$)—NH) or when Z' comprises carbonyl, Z' is selected from among an amide (—CO—NH—, —CONCH$_S$—) and an ester (—CO—O—), wherein R$^9$ is selected from the group consisting of hydrogen, halogen, C$_{1-6}$alkyl, C$_{1-6}$thioalkyl, C$_{1-6}$alkoxy, C$_{1-6}$thioalkoxy, aryloxy, and amino, which alkyl, thioalkyl, alkoxy, thioalkoxy or aryloxy group is optionally mono-, di- or tri-substituted and which amino group is optionally mono- or di-substituted, by one or more substituents selected from among halogen, OH, SH, CN, NO$_2$, C$_{1-6}$alkyl, C$_{1-6}$alkoxy, and C$_{1-6}$alkoxycarbonyl.

BRIEF DESCRIPTION OF THE DRAWINGS

The invention is disclosed in more detail by reference to the drawings, although it is understood that the drawings merely represent specific embodiments of the described invention and are not intended to so limit the invention.

DETAILED DESCRIPTION

Figure 1:
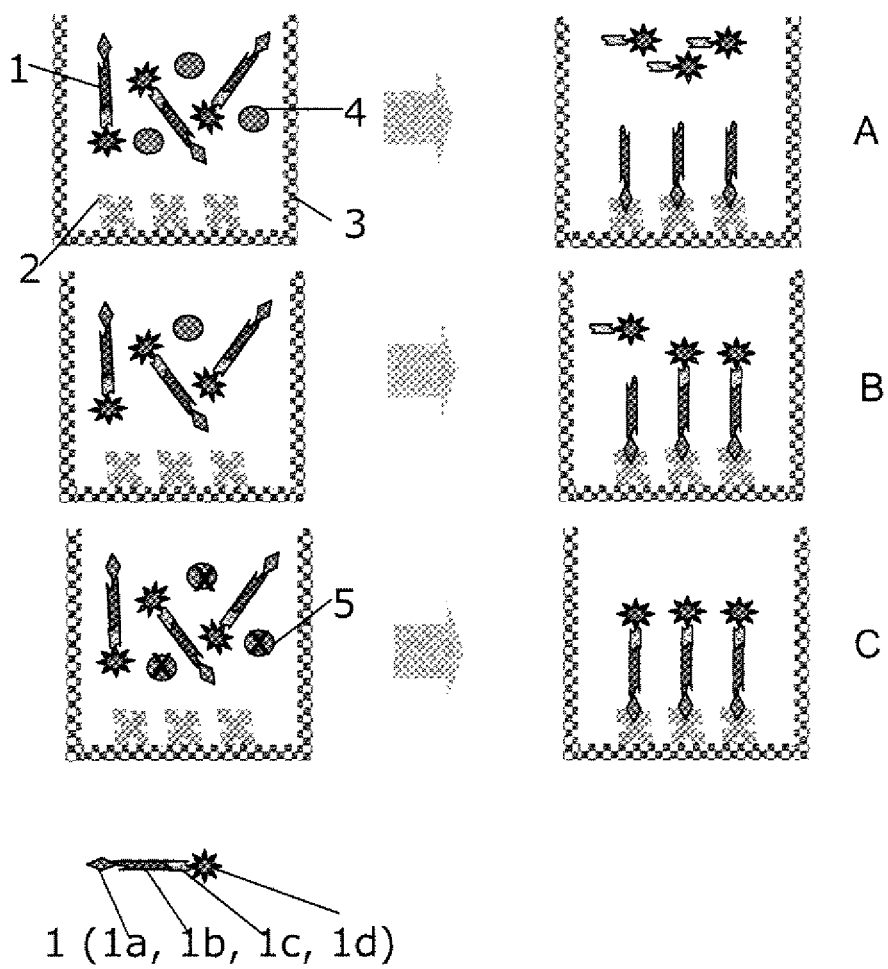
FIG. 1 shows a schematic of a one-step assay method without prior substrate immobilisation.

In the context of this invention a C$_{1-6}$alkyl group means a straight chain or branched chain group of one to six carbon atoms, including but not limited to, methyl, ethyl, propyl, isopropyl, butyl, isobutyl, t-butyl, pentyl, and hexyl. In exemplary embodiments, the C$_{1-6}$alkyl group is methyl, ethyl, propyl or isopropyl.

In the context of this invention a C$_{1-6}$alkylene radical means a straight chain or branched chain radical of one to six carbon atoms, including but not limited to, methylene, ethylene, propylene, isopropylene, butylene, isobutylene, t-butylene, pentylene, and hexylene. In exemplary embodiments, the C$_{1-6}$alkylene group is methylene, ethylene, propylene or isopropylene.

In the context of this invention a C$_{1-6}$alkoxy group means a straight or branched chain group of one to six carbon atoms linked to an oxygen atom, including but not limited to, methoxy, ethoxy, propoxy, isopropoxy, butoxy, isobutoxy, t-butoxy, pentoxy, and hexoxy. In exemplary embodiments, the C$_{1-6}$alkoxy group is methoxy, ethoxy, or propoxy.

In the context of this invention a C$_{1-6}$alkylenoxy radical means a straight or branched chain radical of one to six carbon atoms linked to an oxygen atom, including but not limited to, methylenoxy, ethylenoxy, propylenoxy, isopropylenoxy, butylenoxy, isobutylenoxy, t-butylenoxy, pentylenoxy, and hexylenoxy. In exemplary embodiments, the C$_{1-6}$alkylenoxy group is methylenoxy, ethylenoxy, or propylenoxy.

Amino acid residues in the context of this invention have their conventional three-letter abbreviations. Thus, Ahx stands for 2-amino hexanoic acid (norleucine), Ala stands for alanine, Arg stands for arginine, Asn stands for asparagine, Asp stands for aspartic acid, Aze stands for azetidine-2-carboxylic acid, Cys stands for cysteine, Gln stands for glutamine, Glu stands for glutamic acid, Gly stands for glycine, His stands for histidine, Ile stands for isoleucine, Leu stands for leucine, Lys stands for lysine, Met stands for methionine, Phe stands for phenylalanine, Pip stands for piperidine-2-carboxylic acid, Pro stands for proline, Ser stands for serine, Thr stands for threonine, Trp stands for tryptophane, Tyr stands for tyrosine, and Val stands for valine. p In the context of this invention halogen represents fluoro, chloro, bromo or iodo.

The substrate according to the invention must be able to be attached to an immobilisation matrix in order to separate cleaved from non-cleaved/intact substrates. Thus the substrate according to the invention is terminated by a first partner of a binding pair, which in turn binds to a second partner of the binding pair. This second partner of said binding pair is immobilised on an immobilisation matrix.

The substrate according to the invention can be quickly cleaved by thrombin with excellent specificity. Its central part is a small peptide, in terms of a tri- or tetra-peptide, which is cleaved by thrombin at the scissile bond located between the Arg-moiety and the Z-moiety.

The substrate according to the invention can be used when the sample is, for example, plasma and is particularly advantageous as it is suitable when the sample is, for example, whole blood, because the substrate, due to the chelate technology employed, can be detected at 615 nm.

In an embodiment according to the invention, the substrate is one, wherein X' is absent, Phe is D-Phe, and Arg is L-Arg.

In an embodiment of the invention, X is D-Phe-L-2-Aze-L-Arg or D-Phe-L-2-Pip-L-Arg.

These substrates have shown to provide rapid cleavage kinetics and/or they are highly specific for thrombin.

In an embodiment of the invention, Z' is N and R is arylene, C$_{1-6}$alkylene-arylene, or R$^1{}_a$-arylene-(NHCO—R$^2$)$_b$, wherein R$^1$ and R$^2$ are as defined above and a and b are independently 0, 1 or 2.

Thus, substrates, wherein Z at the scissile bond comprises an aromatic moiety, have shown to provide excellent and rapid cleavage kinetics.

In an embodiment of the invention, Z' is a 6-substituted-1,3,5-triazine-2,4-diamine (NH—(R$^9$C$_3$N$_3$)—NH) or (S—(R$^9$C$_3$N$_3$)—NH) bond, wherein R$^9$ is selected from the group consisting of chloro, fluoro, ethoxy, 2-methoxyethoxy, 2-cyanoethoxy, 2,2,2-trifluoroethoxy, thiophenoxy and ethoxycarbonylthiomethoxy.

Substrates according to this embodiment of the invention are especially specific for thrombin.

In an embodiment according to the invention, the luminescent chelate is a fluorescent lanthanide chelate e.g., as disclosed in U.S. Pat. No. 7,018,851 B2. Such luminescent lanthanide chelates provide high absorptivity at a suitable wavelength, several separate UV absorbing parts in the same ligand structure, effective energy transfer from the UV absorbing part to the lanthanide ion, a strongly chelating part to create thermodynamic stability and high kinetic stability, and a functional group allowing effective coupling of the chelate to be used as a binding reactant without destroying its binding properties, and thus are suitable for the present invention.

In an exemplary embodiment according to the invention, the lanthanide chelates A or A' are selected from:

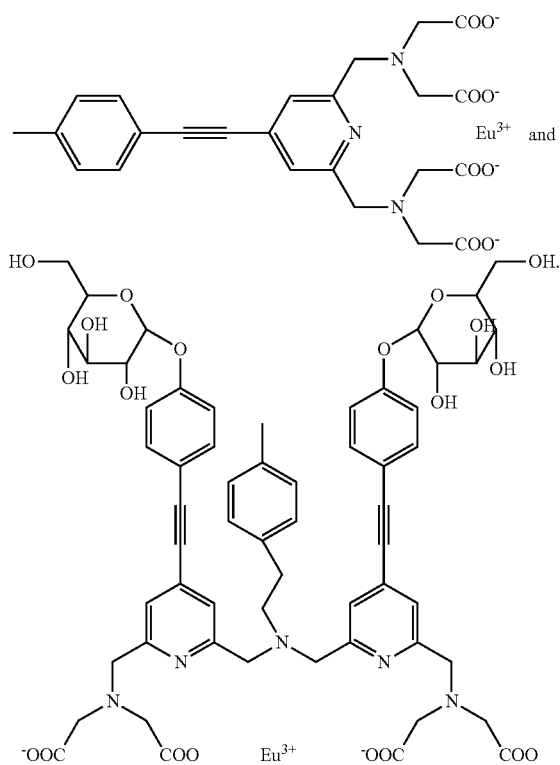

Further, such chelates may include, for example, but are not limited to, stable chelates composed of derivatives of pyridine; bipyridines, terpyridines and various phenolic compounds as the energy mediating groups and polycarboxylic acids as chelating parts. In addition, various dicarboxylate derivatives, macrocyclic cryptates, calixarenes, DTPA carbostril 124 conjugate and macrocyclic Schiff bases have been disclosed in patent applications and/or patents.

In an embodiment of the invention, the binding pair is selected among biotin as the first partner and streptavidin as the second partner (biotin/streptavidin). In other particular embodiments, the binding pair is selected from biotin/avidin, biotin/biotin acceptor peptide, and streptavidin derivative/acceptor peptide.

The above list of binding pairs is non-exhaustive. Generally, the binding pair comprises any binding pair capable of immobilising the substrate according to the invention to an immobilisation matrix. Examples of commercially available binding pairs include, but are not limited to, Strep-tag or Strep-tagII/Strep-Tactin or Biotin/Biotin acceptor peptide.

In a particular embodiment, the first partner is biotin.

In a particular embodiment, the second partner is streptavidin.

Immobilisation matrixes are known to a person skilled in the art and include micro wells, micro particles such as beads, e.g., those made of glass or plastic materials such as, but not limited to, polystyrene or polypropylene.

In an embodiment according to the invention the first partner of a binding pair is connected to the remaining part of the substrate via a spacer. A spacer can result in an improved solubility of the substrate, which is particularly useful for steric reasons. Thus the role of the spacer is to solubilise the peptide/linker/chelate part of the substrate in order to reduce steric hindrance otherwise imposed on the thrombin enzyme.

In an embodiment according to the invention, the spacer is of the formula $NH-R^{10}-CONH-R^{11}-CO-(NH-R^{12}-NH)_i$, wherein each of $R^{10}$, $R^{11}$ and $R^{12}$ is independently selected from among $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, arylene and arylene-$C_{1-6}$alkylene, wherein arylene is phenylene, biphenylene or naphthylene, which phenylene, biphenylene or naphthylene is optionally mono-, di- or tri-substituted by one or more substituents selected from among halogen, OH, SH, CN, $NO_2$, $C_{1-6}$alkyl, $C_{1-6}$alkoxy and $C_{1-6}$alkoxycarbonyl, wherein i is an integer from 0 to 6.

In an embodiment according to the invention, $R^{10}$, $R^{11}$ and $R^{12}$ are identical or different straight-chained $C_{1-6}$alkylene, arylene or arylene-$C_{1-6}$alkylene, and i is 0 or 1.

Alternatively, the spacer is a W-mer peptide, wherein W is an integer from 1 to 40.

In a particular embodiment, the substrates according to the invention are selected from among:

S1V6a

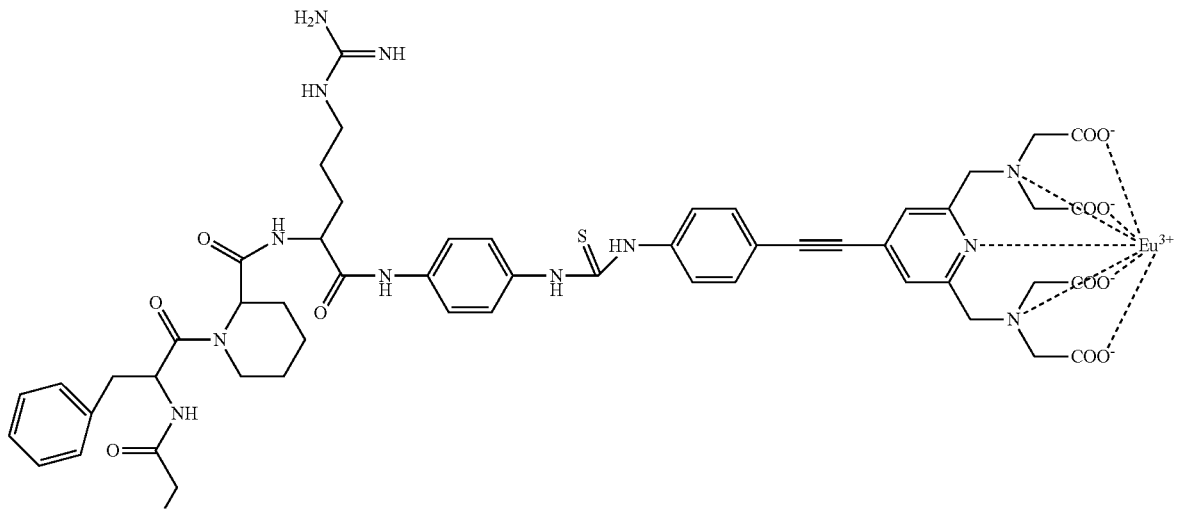

-continued
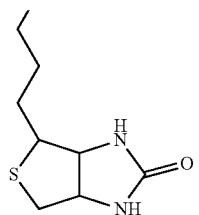
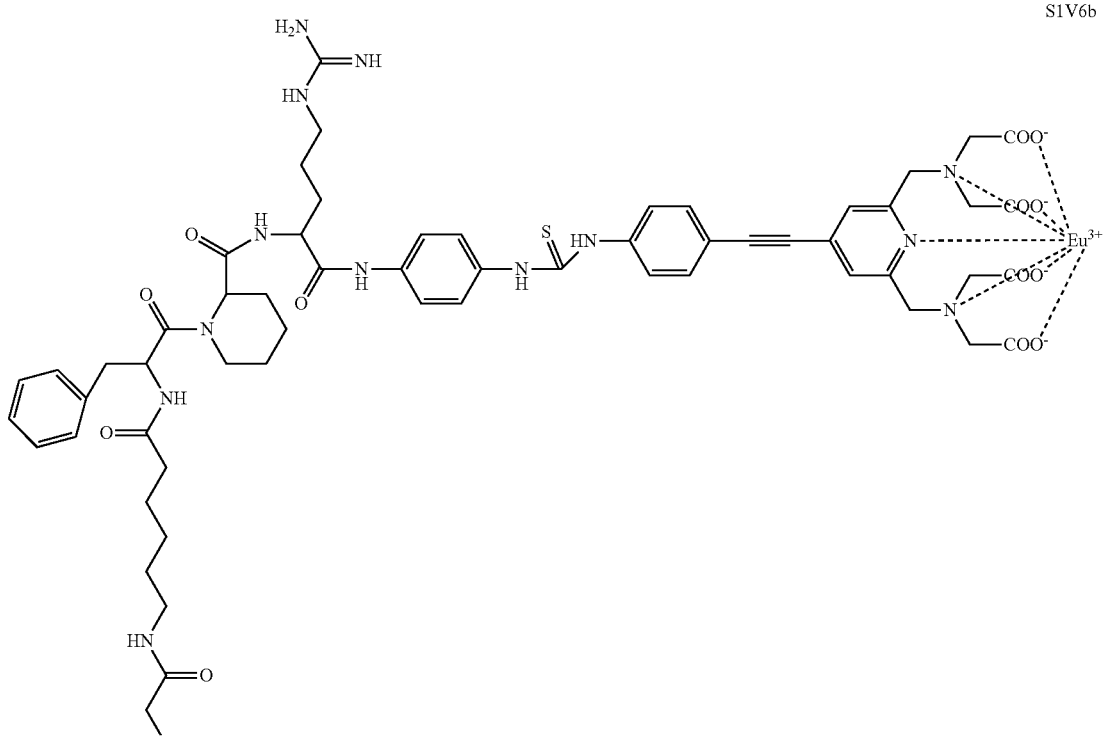
S1V6b
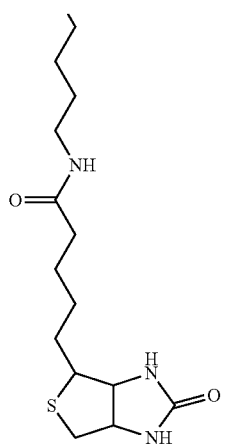

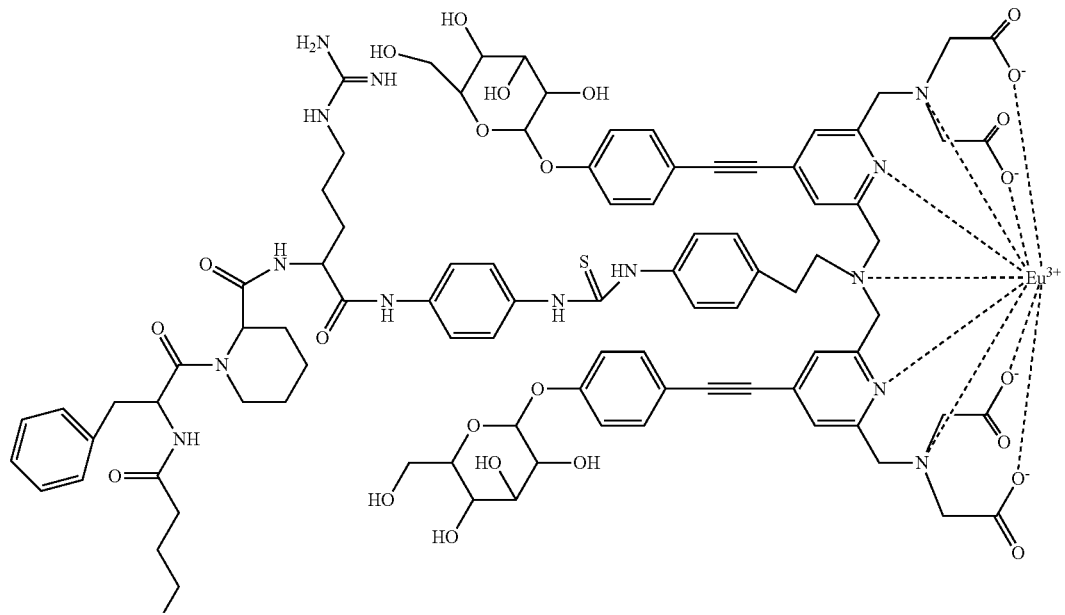
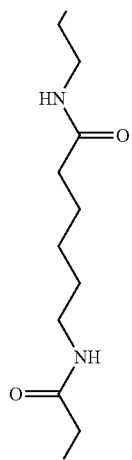
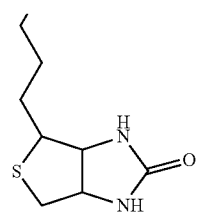

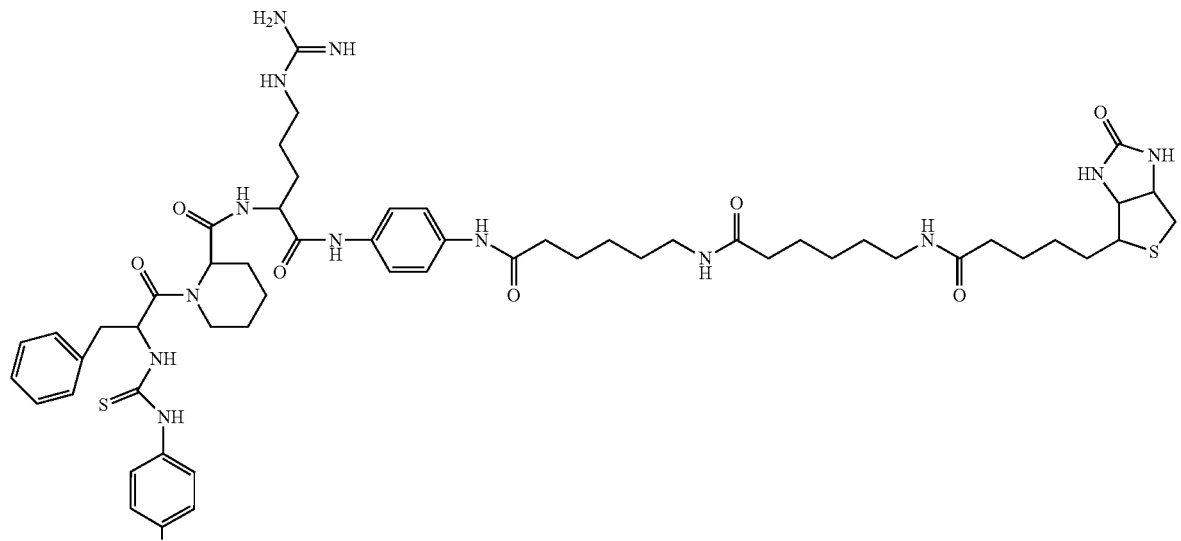
S1V8
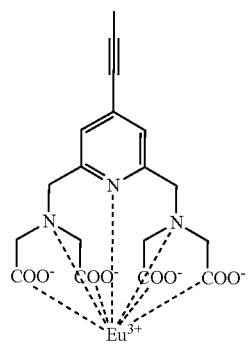
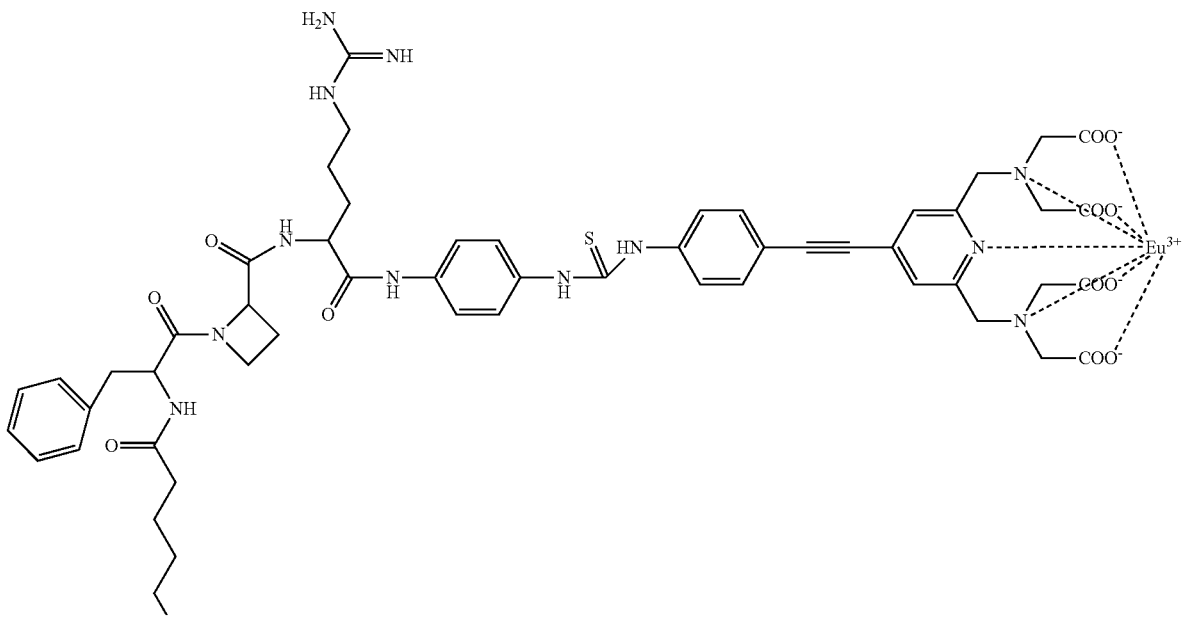
S1V9a

-continued
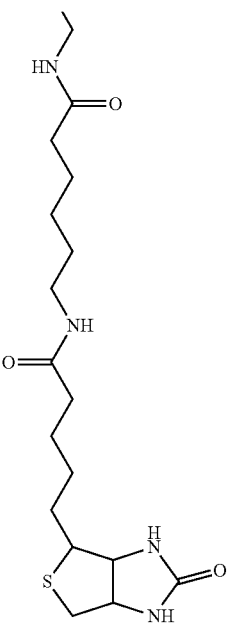
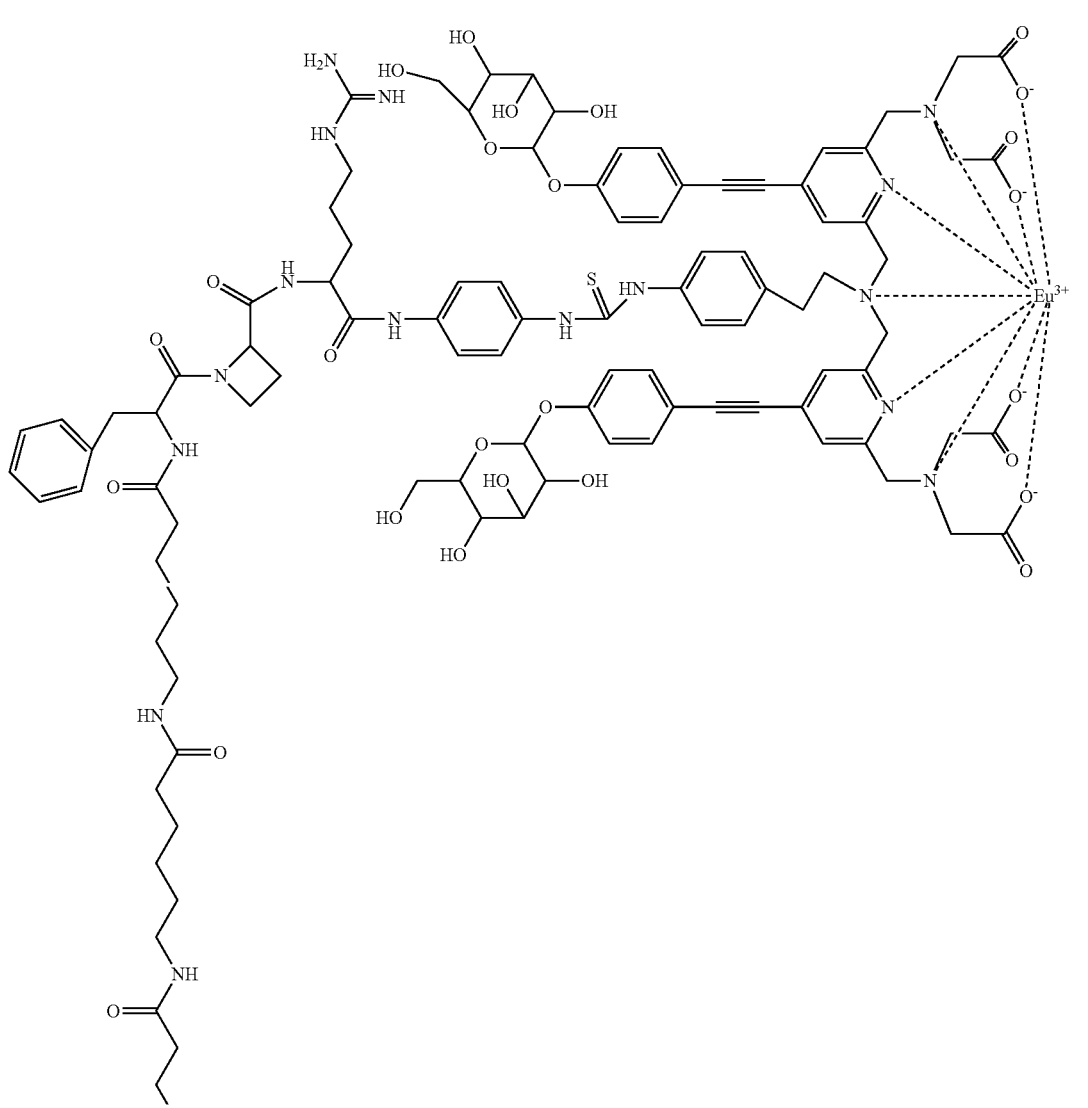

-continued
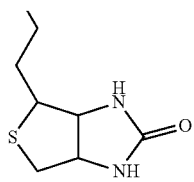
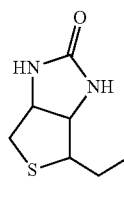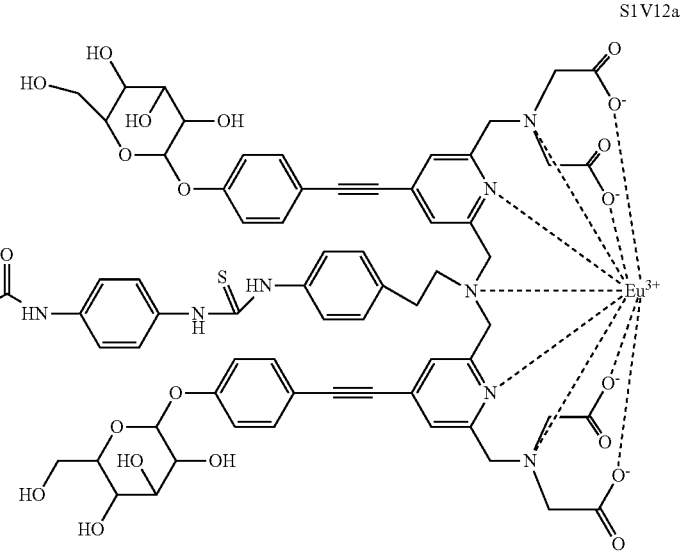
S1V12a
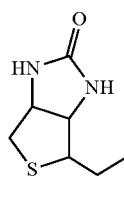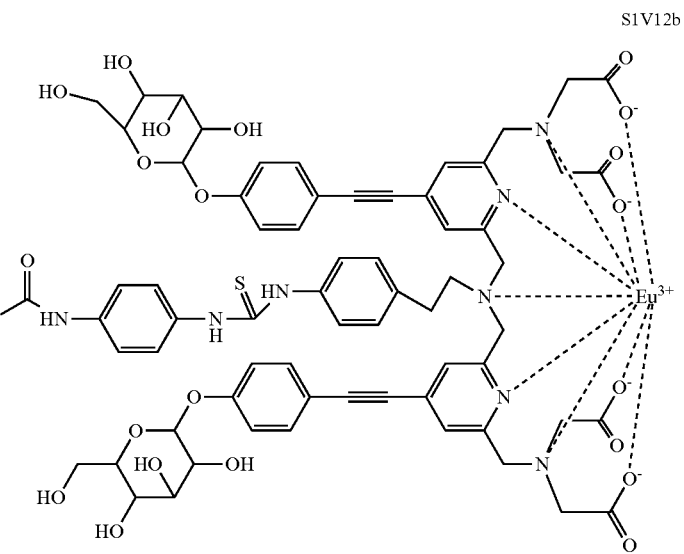
S1V12b

-continued

S1V12c

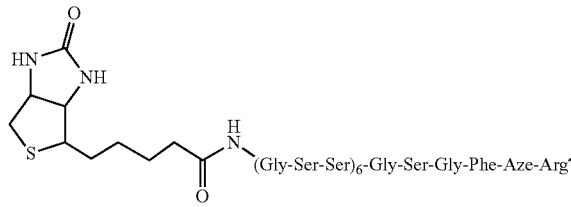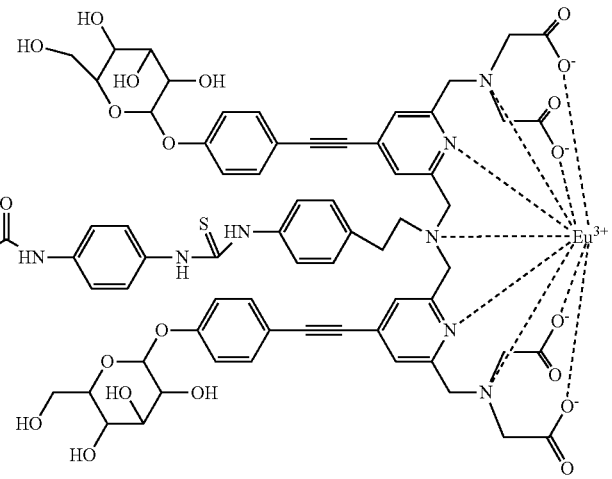

The substrate according to the invention can be used in an assay which is rapid, simple and easy to perform, subject to low variability, easily automated, and of low cost.

As the substrate of the subject invention provides for rapid and precise assays, compared to assays described in the prior art, the assay according to the invention does not require measurement of the time that is needed for absorbance to reach a certain value arbitrarily determined. Instead, assay time can be fixed at a shorter time compared to prior art assays and the luminescence signal measured with time-resolved luminometry. In a preferred embodiment said luminometry is fluorometry. Even at this shorter time, a more precise result is obtained. The end-point can, for example, refer to the time that is necessary to reach a state in which about 80% of the substrate molecules are cleaved by thrombin in the presence of an activator in a normal sample.

Alternatively, the end-point can also refer to the time that is necessary to reach a steady state of the cleavage reaction by thrombin in a normal sample.

By washing off non-immobilised, thrombin-cleaved chelate-containing substrate fragments and non-immobilised, non-thrombin-cleaved substrate, the latter being present when the binding capacity of the immobilisation matrix is less than the amount of substrate molecules, it is possible to directly correlate the reduction of luminescence emission in the sample compared to the luminescence from a thrombin-free standard sample (cleavage percentage) with the thrombin activity in the sample.

Alternatively, a substrate is immobilised onto the surface of an immobilisation matrix, such as a micro well or a micro particle. Sequentially, simultaneously or substantially simultaneously, a test sample, such as, for example, whole blood or plasma, together with an activator, is added to the immobilisation matrix. The resulting reaction mixture is incubated to enable thrombin to act on the substrate, leading to the release of thrombin-cleaved, chelate-containing substrate fragments and leaving the binding partner-containing substrate fragment and non-thrombin-cleaved intact substrate still on the immobilisation matrix.

The identity of the activator used depends on the parameter PR, APTT or ACT to be determined. Non-limiting examples of activators to be used include thromboplastin, a partial thromboplastin reagent such as a phospholipid and contact activators such as silica, kaolin, celite, ellagic acid etc.

The amount of bioactive thrombin, i.e., thrombin not bound to any inhibitor (e.g., antithrombin) and thus active in proteolytic activity, in the unknown sample can be determined from a standard curve for bioactive thrombin by its cleavage percentage (a decrease in luminescence intensity relative to total luminescence intensity). Subsequently, the level of bioactive thrombin can be expressed as the ratio of bioactive thrombin from a group of normal samples (n≧20) to that from an unknown sample. This ratio is equivalent to either prothrombin time ratio (PR), if the activator used is thromboplastin, or activated partial thromboplastin time (APTT) ratio, if the activator used is a partial thromboplastin reagent (e.g., a phospholipid) and contact activator (e.g., silica, kaolin, celite, or ellagic acid), or activated clotting time (ACT) ratio, if the activator used is a contact activator and the sample type used is native whole blood.

In an embodiment of the invention, the addition of the test sample and activator is performed simultaneously or substantially simultaneously with the addition of the substrate to an immobilisation matrix.

The one-step assay method without prior substrate immobilisation is shown schematically in FIG. 1. FIG. 1 is described in detail below.

This method is particularly useful when the substrate in question is not easily cleavable when immobilised on the immobilisation matrix, but is cleavable by thrombin in the liquid phase, i.e., when the cleavage kinetics of the substrate in the liquid phase is faster than or at least equally fast as the binding partner binding kinetics. Thus, both the cleavage reaction between the substrate and thrombin molecules and the binding reaction between immobilised binding partner and cleaved as well as intact substrate molecules take place during the following incubation step.

Figure 2:
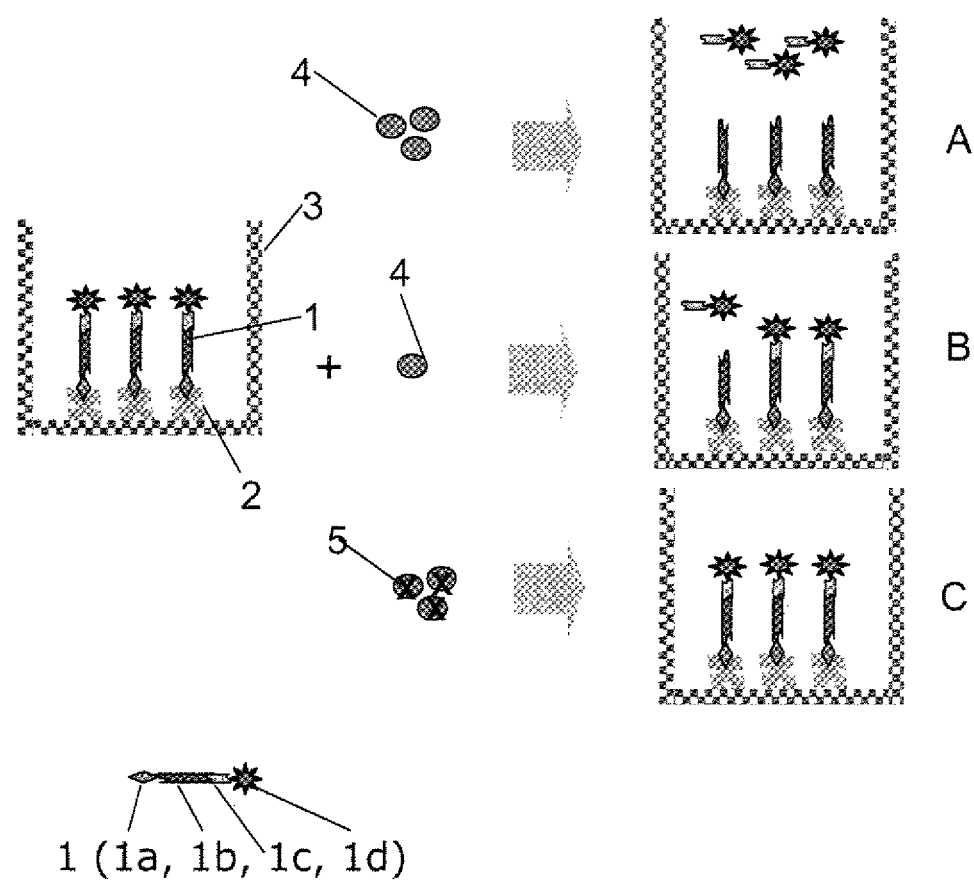
FIG. 2 shows a schematic of a one-step assay method with prior substrate immobilisation.

In another embodiment of the invention, the addition of the test sample is performed after immobilisation of the substrate to an immobilisation matrix. The one-step assay method with prior substrate immobilisation is shown schematically in FIG. 2. FIG. 2 is described in detail below.

Such an assay has many advantages such as simplicity, rapidity and robustness. However, a condition thought to be a prerequisite for this embodiment is that substrates should be cleavable when immobilised on the immobilisation matrix.

Subsequently, non-immobilised, thrombin-cleaved chelate-containing substrate fragments are washed off. The luminescence emission from the immobilised intact substrate is measured and compared to the luminescence from a thrombin-free standard sample. The percentage of luminescence intensity reduction in the sample (cleavage percentage) is directly correlated with the thrombin activity in the sample.

Figure 3:
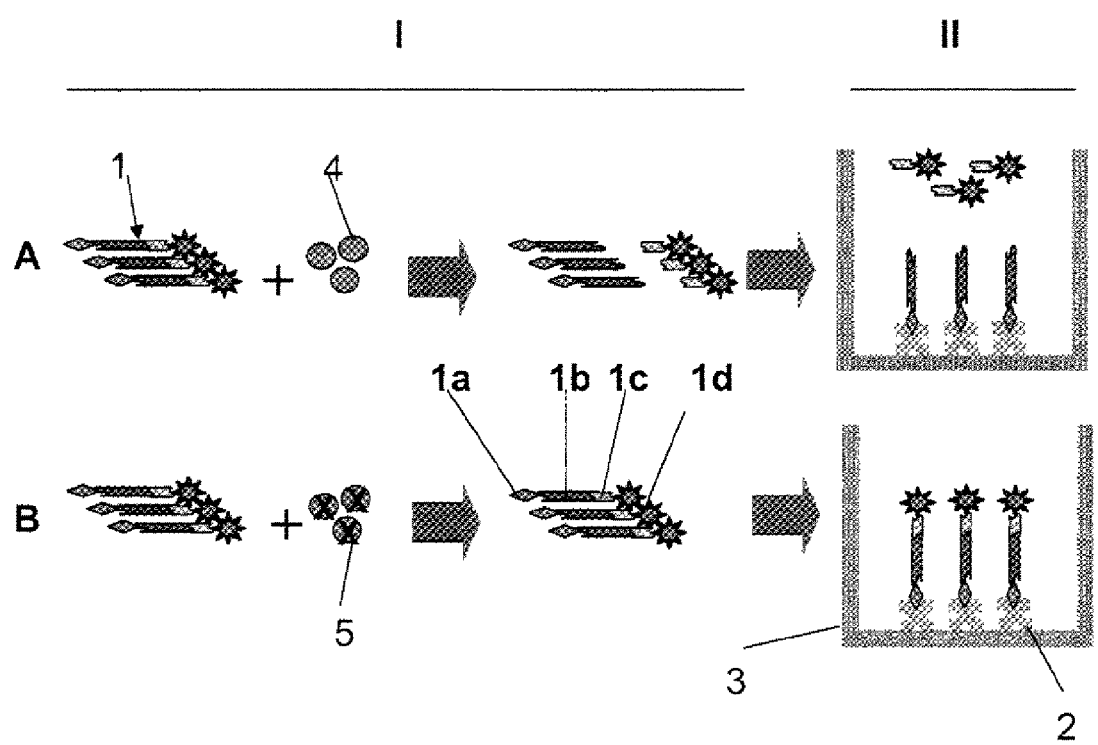
FIG. 3 shows a schematic of a two-step assay method.

The two-step assay can advantageously be utilised when the substrate in question performs well only in the liquid phase. The two-step assay is shown schematically in FIG. 3. FIG. 3 is described in detail below.

In this embodiment, a reaction mixture comprising a test sample, such as plasma or whole blood, an activator and a substrate is reacted in the liquid phase. Subsequently, part or all of said reaction mixture is transferred to an immobilisation matrix, where immobilisation of thrombin-cleaved substrate fragments and non-thrombin-cleaved intact thrombin takes place. After washing off thrombin-cleaved chelate-containing substrate fragments and non-immobilised, non-thrombin-cleaved substrate, the level of luminescence from immobilised intact substrate is measured as above.

Which type of assay is chosen (such as a one-step or two-step assay) mainly depends on how difficult it is to perform a simultaneous addition of substrate, activator and sample to an immobilisation matrix. When it is difficult, a two-step assay is preferably used. When it is not difficult, a one-step assay can be used. Besides, the two-step assay has the advantage over the one-step assay that the substrate amount applied can be very high as long as substrate solubility permits.

Another aspect of the present invention provides the use of a substrate according to the invention for determining the level of bioactive thrombin in a sample. The substrates according to the invention display excellent specificity for thrombin and can be quickly cleaved by thrombin, thus allowing the use of said substrates in an assay which is easy to perform, which can be automated and which provides reliable results in a short time.

In an embodiment, the present substrate is adopted specifically for the thrombin case, but it may as well be applied with different enzymes since the combination of a tri- or tetra-peptide (X) and the subject linker (Z) may be easily cleaved by other enzymes as well.

Thus, the substrate according to the present invention may be adapted to the desired application by a minor modification of the substrate, more specifically, by the choice of the peptide.

Different coagulation factors can be determined, such as active and inactive forms of FII, FV, FVII, FVIII, FIX, FX, FXI, and FXII, as well as the active and inactive forms, fragments and combinations of C1, C2, C3, C4, C5, C6, C7, C8, and C9. Enzymes such as myeloperoxidase (MPO), alanine amino transferase (ALAT), aspartate amino transferase (ASAT), caspase-1 and glutathione peroxidase-1 (GPx-1) can also be determined.

In FIG. 1, a one-step assay without prior substrate immobilisation is shown schematically. The used substrate 1 comprises 4 parts ((1a, 1b, 1c and 1d) (A-X-Z-A')), wherein 1a denotes the first partner of a binding pair and 1a comprises optionally a spacer, 1b denotes a tri- or tetra-peptide, 1c denotes a linker and 1d denotes a luminescent chelate. 2 denotes the second partner of the binding pair bound to the surface of an immobilisation matrix 3. 4 denotes the presence of thrombin in the test sample (A with a high level and B with a low level of thrombin) and 5 denotes a thrombin free test sample (C).

In A, which represents a high level of thrombin, the substrate 1 reacts with the test sample 4. This results in a cleaved substrate. The cleaved substrate comprises two parts: a first part (1a, 1b) and a second part (1c, 1d). (1a, 1b) immobilises to the immobilisation matrix, while the second part (1c, 1d) of the substrate is washed away. Then, the emission of luminescence from immobilised intact substrate (1a, 1b) is measured and compared to the luminescence of a thrombin free sample 5 (C). The washing and measurement steps are not shown in FIG. 1.

FIG. 1 also illustrates the one-step assay with a low thrombin level (shown in B) and with a zero thrombin level (shown in C). C is used as the control.

FIG. 2 illustrates a one-step assay as described above, but where the addition of the test sample 4 or 5 is performed after immobilisation of the substrate 1 according to the invention to the immobilisation matrix 3.

FIG. 3 illustrates a two-step assay. The first step (I) shows that substrate 1 reacts with the test sample 4 (with thrombin (A)) or 5 (free of thrombin (B)). This results in a thrombin cleaved substrate (A) or in an intact substrate (B). In step II, a part or all of the reaction mixture is transferred to an immobilisation matrix, where immobilisation of the thrombin-cleaved substrate fragment (1a, 1b) (A) and non-thrombin-cleaved intact thrombin substrate 1 (1a, 1b, 1c and 1d) (B) takes place. After washing off the thrombin-cleaved chelate-containing substrate fragment (1c, 1d), the emission of luminescence from the immobilised intact substrate 1 is measured as in the one step assay. The washing and measurements steps are not shown in FIG. 3.

Thus, with (A) a low level of chelate (luminescence/fluorescence) is measured, which represent a high level of thrombin. In contrast, with (B) a high level of chelate (luminescence/fluorescence) is measured, reflecting the absence of thrombin.

EXAMPLES

The present invention is described in more detail in the following, non-limiting specific examples.

For the below examples, the following materials and instrumentation were used.

Materials

Sulfo-NHS-LC-LC-Biotin was purchased from Pierce, p-phenylenediamine was purchased from Acros, (7-azabenzotriazol-1-yloxy)tripyrrolidinophosphonium hexafluorophosphate (PyAOP) was purchased from Aldrich and N-ethyldiisopropylamine (DIPEA) was purchased from Fluka. Trifluoroacetic acid (TFA) was purchased from Riedel-de Haën and triethylammonium acetate buffer (TEAA) was purchased from Fluka. Acetonitrile (MeCN) was HPLC grade from J. T. Baker. DMF was purchased from Lab-Scan and dried over molecular sieves (4 Å). All other chemicals used were of analytical grade.

H-Phe(D)-Pip-Arg was purchased from KJ Ross-Petersen ApS. N-terminally-biotinylated long peptide-based D-Phe-L-Aze-Arg-OH such as Biotin-(Ser-(Gly)$_2$)$_7$ D-Phe-L-Aze-Arg-OH were purchased from Invitrogen. Innovin was purchased from Dade-Behring, Siemens. Bovine serum albumin (BSA) was purchased from Sigma.

9-dentate europium-chelate(2,2',2'', 2'''-{[2-(4-Isothiocyanatophenyl)-ethylimino]-bis(methylene)bis{4-{[4-(a-galactopyranoxy)phenyl]ethynyl}-pyridine-6,2-diyl}bis(methylenenitrilo)}tetrakis(acetato)europium(III)), wash solution and single cups coated with streptavidin were purchased from Innotrac Diagnostics (Finland).

Low-fluorescence 12-well Maxisorp microtitration strips and single Maxisorp microtitration wells (ultraviolet-quenched) were purchased from Nunc (Denmark).

Instrumentation

Mass spectrometry (MS) was operated on a Voyager DE-PRO (MALDI TOF) from Perseptive Biosystems, using a-cyano-4-hydroxycinnamic acid as matrix. A 1420 multilabel counter (Victor) from Wallac Oy, Perkin-Elmer life Sciences was used to measure time-resolved fluorescence at 615 nm when an assay was manually performed, while an Aio immunoanalyser from Innotrac Diagnostics was used to measure time-resolved fluorescence at 615 nm when an assay was semi-automatically performed.

Example 1

Synthesis of S1V6c

Figure 4:
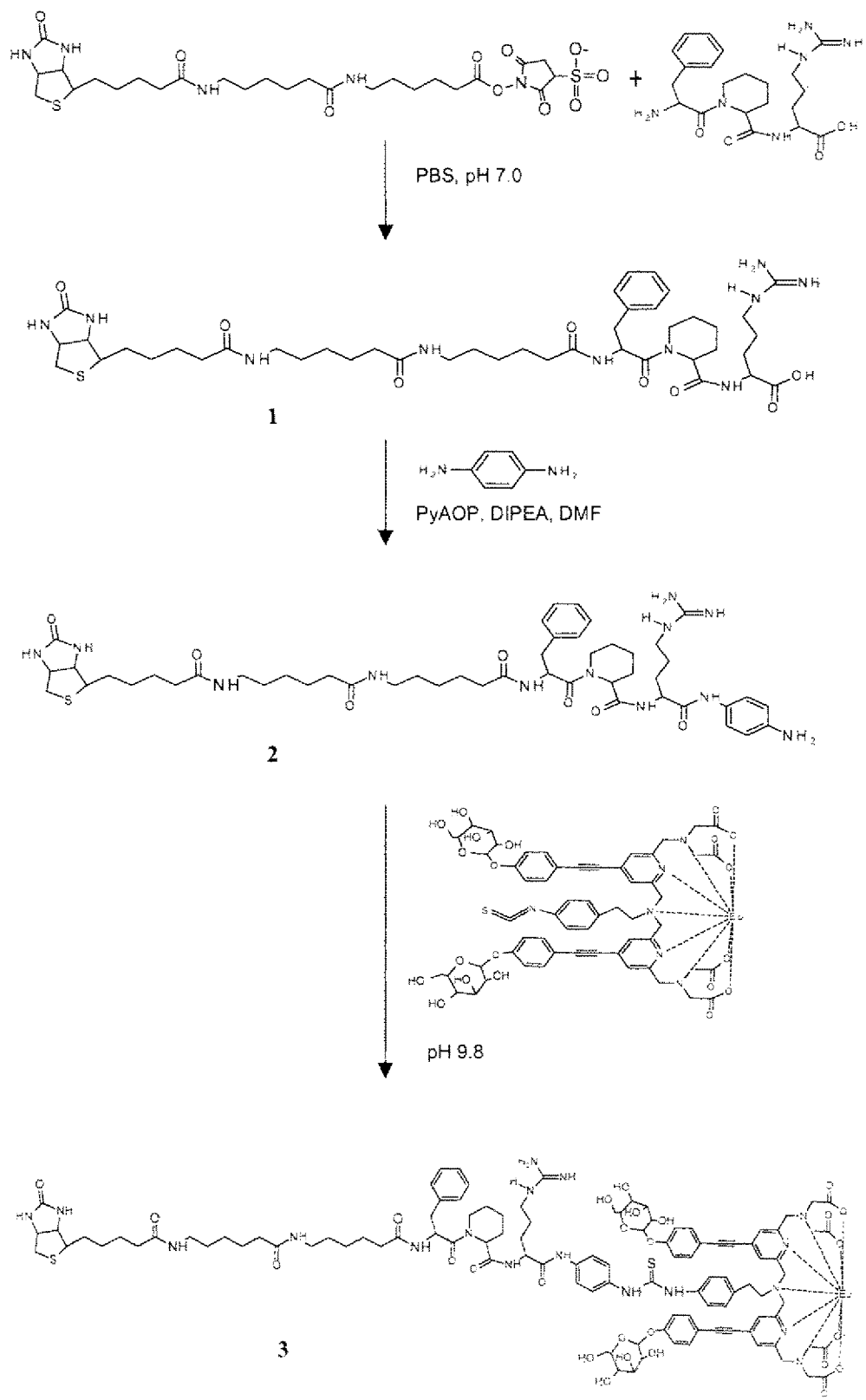
FIG. 4 shows the reaction scheme of the synthesis of S1V6c, a substrate according to the invention.
Figure 5:
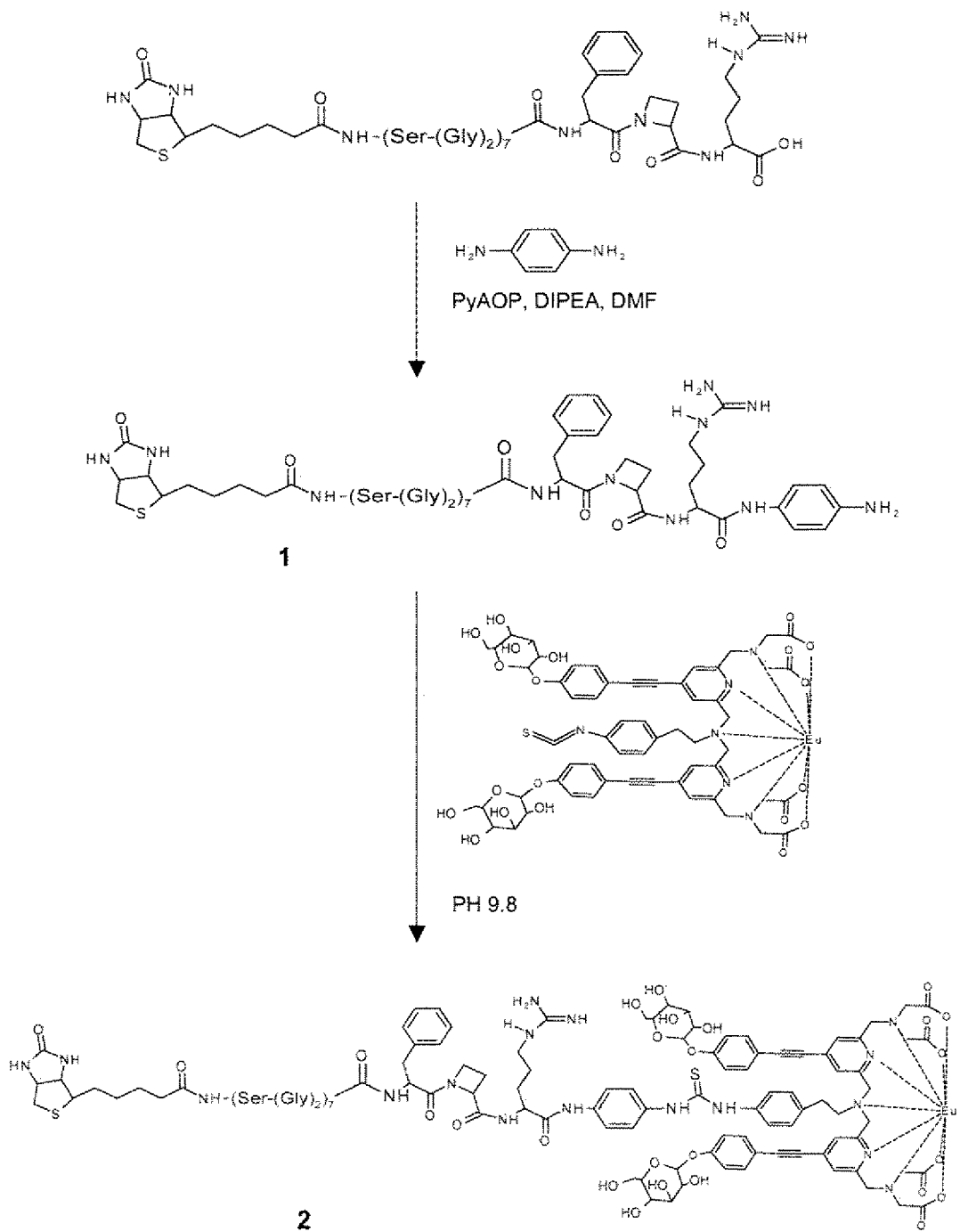
FIG. 5 shows the reaction scheme of the synthesis of S1V12a, another substrate according to the invention.
Figure 6:
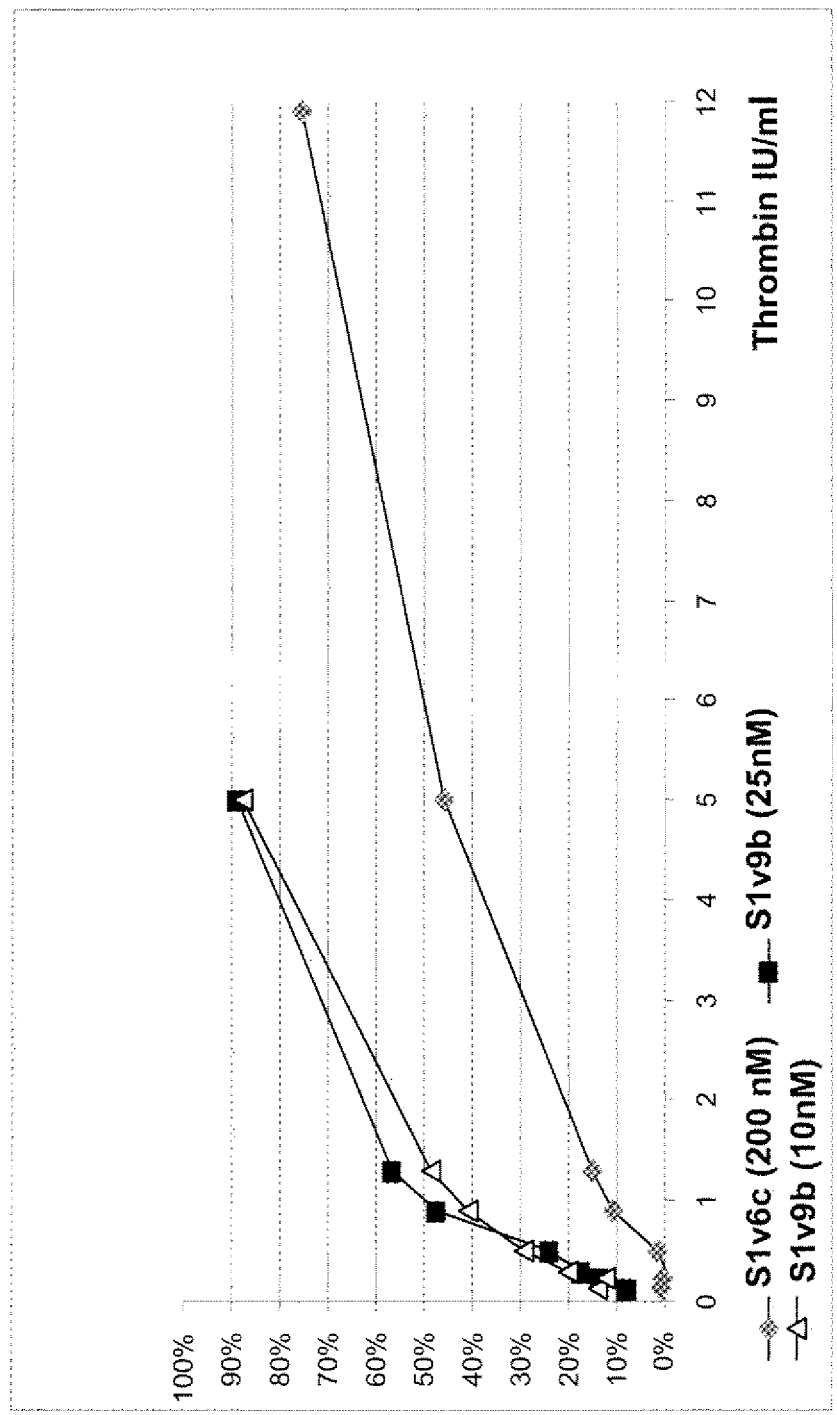
FIG. 6 shows a standard curve of S1V6c and S1v9b according to the invention.

The synthesis of S1V6c involves three steps starting with the use of a tripeptide comprising H-Phe(D)-Pip-Arg-OH as shown in FIG. 4. First, a biotin group with a linear spacer is connected to the N-terminal alpha-amino group of the tripeptide. Then, a diamine linker, such as 4-phenylene-diamine, is coupled to the C-terminal carboxyl group of the tripeptide. Finally, a 9-dentate europium chelate is conjugated to the aromatic amino group of the introduced linker molecule.

Synthesis Procedure i) Biotinylation

H-Phe(D)-Pip-Arg-OH (5.0 mg, 11.6 μmol) was dissolved in PBS-buffer (pH 7.0, 1 ml). Sulfo-NHS-LC-LC-Biotin (12.0 mg, 17.3 μmol) was added and the mixture was stirred overnight at RT. The reaction mixture was purified with HPLC. Yield: 5.5 mg (54%). MS: found 885.67. calculated 885.15.

ii) Coupling of a Diamine-Linker

The biotinylated product from i) (2.4 mg, 2.7 μmol) was dissolved in dry DMF (0.5 ml). 4-Phenylene-diamine (1.2 mg, 10.84 μmol), PyAOP (1.7 mg, 3.3 μmol) and DIPEA (0.6 μl, 3.3 μmol) were added and the mixture was stirred overnight at RT. DMF was evaporated and the reaction mixture was purified on a HPLC Column of Thermo ODS Hypersil (size: 150×10 mm). A linear gradient made from A (0.1% TFA) and B (MeCN) in 20 minutes from 5% B to 50% B was used for elution with a flow rate of 2.5 ml/min. The yield was 2.4 mg (92%). MS found (975.83) was in close agreement with MS calculated (975.28).

iii) Labelling

The product from ii) (2.0 mg, 2.1 μmol) was dissolved in 50 mM carbonate buffer (pH 9.8, 0.5 ml). 9-dentate europium-chelate (2,2',2'', 2'''-{[2-(4-Isothiocyanatophenyl)-ethylimino]-bis(methylene)bis{4-{[4-a-galactopyranoxy)phenyl]ethynyl}-pyridine-6,2-diyl}bis(methylenenitrilo)}tetrakis(acetato)europium(III)) (3.3 mg, 2.5 μmol) was added and the reaction was stirred overnight at RT. The reaction mixture was purified on a HPLC Column of Phenomenex C18 (size: 250×10 mm). A linear gradient made from A (20 mM TEAA) and B (20 mM TEAA+50% MeCN) in 30 minutes from 5% B to 100% B was used for elution with a flow rate of 3 ml/min. The yield was 1.3 mg (27%).

Example 2

Synthesis of S1V12a

The synthesis of S1V12a involves only two steps (see FIG. 5) as the starting material already contains a biotin group and a spacer group made of amino acids. After the same diamine linker, i.e., 4-phenylene-diamine is coupled to the C-terminal carboxyl group of the tripeptide, a 9-dentate europium chelate is conjugated to the aromatic amino group of the introduced diamine linker molecule. The experimental conditions used for the synthesis of S1V12a were the same as those used in the relevant steps for the synthesis of S1V6c.

Example 3

Three different reference standard curves to be used in subsequent thrombin determinations were constructed.

Standard curve A represents S1V6c in a concentration of 200 nM. Standard curve B represents S1V9b in a concentration of 10 nM. Standard curve C represents S1V9b in a concentration of 25 mM. The substrates are prepared according to the conditions described in example 1.

Recombinant thromboplastin (Innovin) was used as an activator. The assay buffer was a conventional HEPES buffer.

Standards of thrombin concentrations from 0 to 11.9 IU/ml were applied.

The assay was performed as a two-step assay. In step I, the thrombin containing standards were added in different thrombin concentrations to the assay buffer together with an activator and the substrate. The reagents were mixed well and incubated at 37° C. for minutes.

In step II, a part of the reaction mixture was transferred to a micro well where the capture took place. The substrate was allowed to immobilise/capture to the micro well for approximately 3 min at 37° C. before washing and drying. Non-captured substrate as well as the chelate containing cleaved substrate was washed away and the micro well was then dried. Finally fluorescence counts from the dried micro well were measured with a fluorescence counter.

The detected fluorescence counts were compared with a control sample free of thrombin and for constitution of the standard curve, the reduction in signal compared to the reference (free of thrombin) was calculated.

The results shown in FIG. 6, demonstrate that increasing concentrations of S1V6c and S1V9b result in an increased reduction of signal. This demonstrates that the substrate S1V6c and S1V9b are both very effective substrates for thrombin. S1V9b resulted in a higher signal reduction at lower thrombin concentration compared to S1V6b. Still however, both substrates are suitable thrombin substrates and both can therefore be used for determining the level of thrombin in a sample.

Example 4

For measurements in whole blood, the standard curve in example 3 may be applied subject to the correction for the whole blood hematocrit value. Whole blood samples as well as plasma samples from 2 healthy female test persons, were tested for thrombin according to the invention.

Four independent measurements on a plasma sample from test person one, showed a reduction in the detected signal compared to the control signal of 87.7%±0.5%. For test person two, the reduction was 91.5%±0.1%.

Similar results were obtained with whole blood samples, 80.7%±0.9% and 86.3%±0.2%, respectively, for test person one and for test person two.

The results demonstrate the ability of the substrate and the assay according to the invention to measure thrombin in whole blood as well as in plasma samples and the invariability thereof.

Without further description, it is believed that one of ordinary skill in the art can, using the preceding description and the illustrative examples, make and utilize the present invention and practice the claimed methods. All patents, patent applications and other references cited throughout this application are herein incorporated by reference in their entirety.

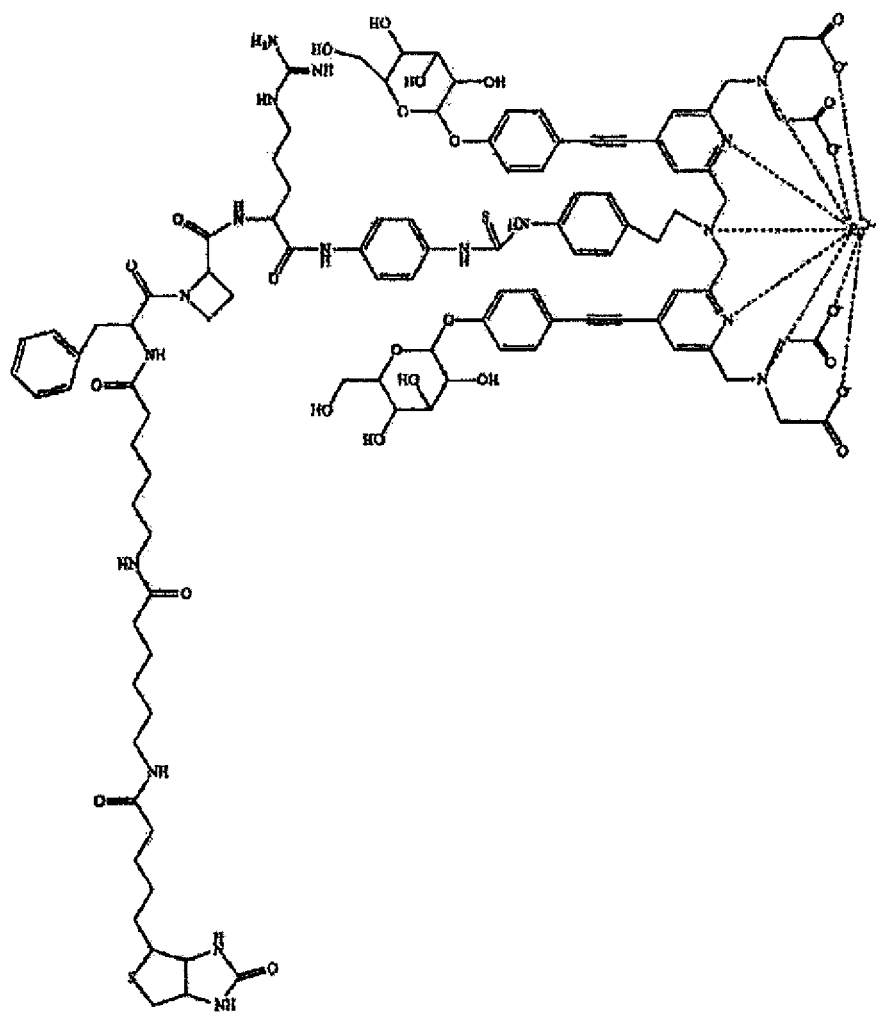

The invention claimed is:

1. A substrate for thrombin having the formula:

A-X—Z-A' wherein
one of either A or A' comprises a luminescent chelate, and the other one of A or A' comprises a first partner of a binding pair, optionally including a spacer, and connected via a peptide bond to the remaining part of the substrate;

X forms a tri- or tetra-peptide selected from the group consisting of X'- Phe-Aze-Arg, X'-Phe-Pip-Arg, and X'-Phe-Pro-Arg, wherein X' is absent or is selected from the group consisting of Lys, Ahx, Ile, and Val;

Z is NH—R—Z', wherein
R is selected from the group consisting of $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, $C_{1-6}$alkylenoxy-carbonyl, $C_{1-6}$alkylene-arylene, $C_{1-6}$alkylenoxy-arylene, $C_{1-6}$alkylene-NH, $C_{1-6}$alkylenoxy-NH, $C_{1-6}$alkylene-NHCO, $C_{1-6}$alkylenoxy-NHCO, $C_{1-6}$alkylene-CONH, $C_{1-6}$alkylenoxy-CONH, $C_{1-6}$alkylene-COS, $C_{1-6}$alkylenoxy-COS, $C_{1-6}$alkylene-CONH -$C_{1-6}$alkylene-arylene, arylene, arylene-$C_{1-6}$alkylene, arylene-$C_{1-6}$alkylenoxy, $(R^1)_a$-arylene-$(NHCO—R^2)_b$, $(R^3)_c$-arylene-$(CONH—R^4)_d$, $(R^5—CONH)_e$-arylene- $(R^6)_f$, and $(R^7-NHCO)_g$-arylene- $(R^8)_h$, wherein each $R^1$, $R^2$, $R^3$, $R^4$, $R^5$, $R^6$, $R^7$, and $R^8$ at each occurrence is independently selected from the group consisting of $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, arylene and arylene-$C_{1-6}$alkylene, and each of a, b, c, d, e, f, g, and h is independently selected from the group consisting of the integers from 0 to 6, wherein the arylene is phenylene, biphenylene or naphthylene, wherein the phenylene, biphenylene or naphthylene is optionally mono- , di- or tri-substituted by one or more substituents selected from the group consisting of halogen, OH, SH, CN, $NO_2$, $C_{1-6}$alkyl, $C_1$-alkoxy, and $C_{1-6}$alkoxycarbonyl;

Z' is selected from the group consisting of thiourea (—NH—CS—NH—), aminoacetamide (—NH—CO—$CH_2$—NH—), amide (—NH—CO—), methylamide (—$NCH_3$—CO—), substituted-triazine-diamine (—NH—($R^9C_3N_3$)—NH—), thioether (—S—), thioacetamide (—S—$CH_2$—CO—NH—), disulfide (—S—S—), (—S—CO—$CH_2$—NH—), (—S—($R^9C_3N_3$)—NH—), amide (—CO—NH—, —CO—$NCH_3$—) and ester (—CO—O—), wherein $R^9$ is selected from the group consisting of hydrogen, halogen, $C_{1-6}$alkyl, $C_{1-6}$thioalkyl, $C_{1-6}$alkoxy, $C_{1-6}$thioalkoxy, aryloxy, and amino, which alkyl, thioalkyl, alkoxy, thioalkoxy or aryloxy group is optionally mono-, di- or tri-substituted and which amino group is optionally mono- or di-substituted by one or more substituents selected from the group consisting of halogen, OH, SH, CN, $NO_2$, $C_{1-6}$alkyl, $C_{1-6}$alkoxy, and $C_{1-6}$alkoxycarbonyl, wherein said first partner of a binding pair is selected from the group consisting of biotin/streptavidin, biotin/avidin, biotin/biotin acceptor peptide, and streptavidin/streptavidin acceptor peptide, and wherein said luminescent chelate is a fluorescent lanthanide chelate selected from the group consisting of

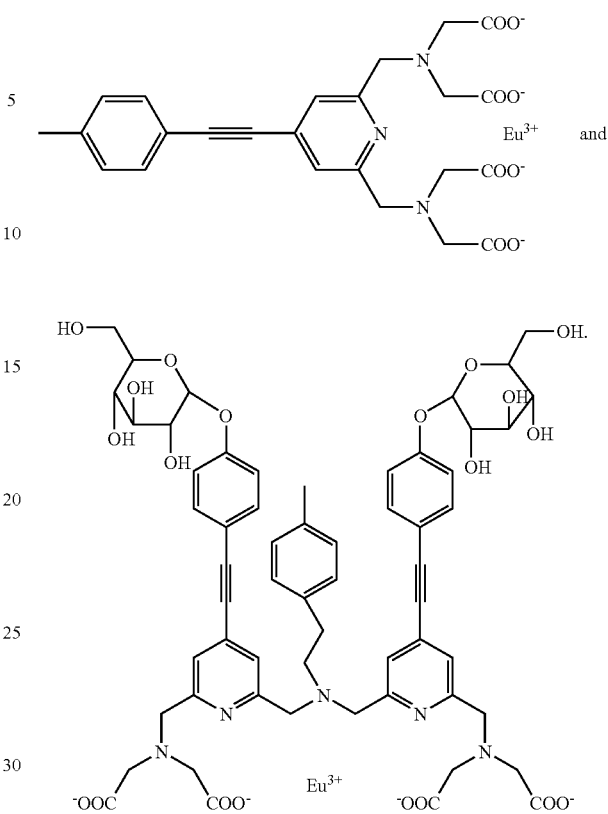

2. The substrate according to claim 1, wherein X is D-Phe-L-2-Aze-L-Arg or D-Phe-L-2-Pip-L-Arg.

3. The substrate according to claim 1, wherein R is arylene, $C_{1-6}$alkylene-arylene, or $(R^1)_a$-arylene-$(NHCO—R^2)_b$, wherein a and b are independently 0, 1 or 2.

4. The substrate according to claim 1, wherein said first partner of a binding pair is connected to the remaining part of the substrate via a spacer of the formula NH—$R^{10}$—CONH—$R^{11}$—CO—(NH—$R^{12}$—NH)$_i$, wherein each of $R^{10}$, $R^{11}$ and $R^{12}$ is independently selected from the group consisting of $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, arylene and arylene-$C_{1-6}$alkylene, wherein the arylene is phenylene, biphenylene or naphthylene, wherein the phenylene, biphenylene or naphthylene is optionally mono-, di- or tri-substituted by one or more substituents selected from the group consisting of halogen, OH, SH, CN, $NO_2$, $C_{1-6}$alkyl, $C_{1-6}$alkoxy, and $C_{1-6}$alkoxycarbonyl, and wherein i is an integer from 0 to 6, or the spacer is a W-mer peptide, wherein W is an integer from 2 to 40.

5. The substrate according to claim 4, wherein $R^{10}$, $R^{11}$ and $R^{12}$ are identical or different straight-chained $C_{1-6}$alkylene, arylene or arylene-$C_{1-6}$alkylene and i is 0 or 1.

6. The substrate according to claim 1 selected from the group consisting of:

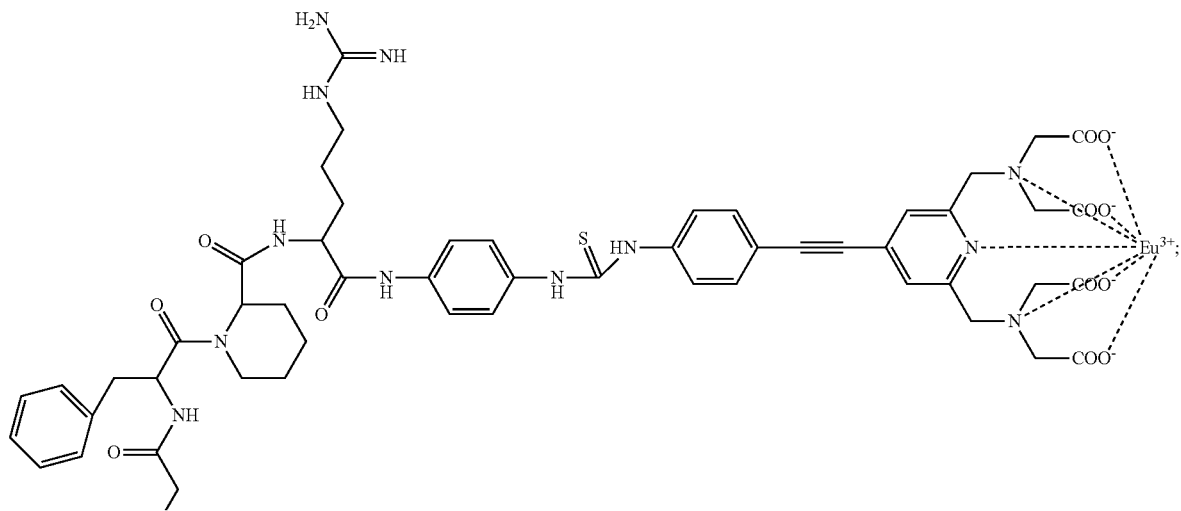
S1V6a
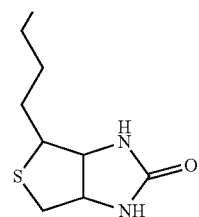
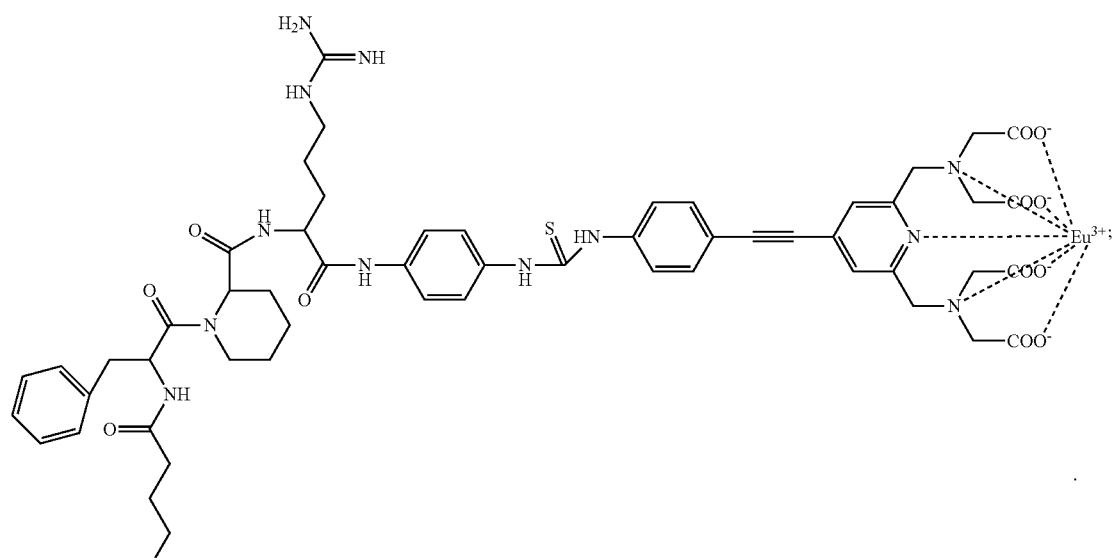
S1V6b

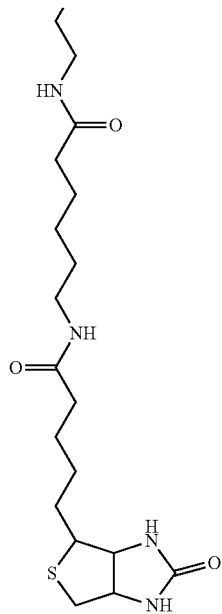
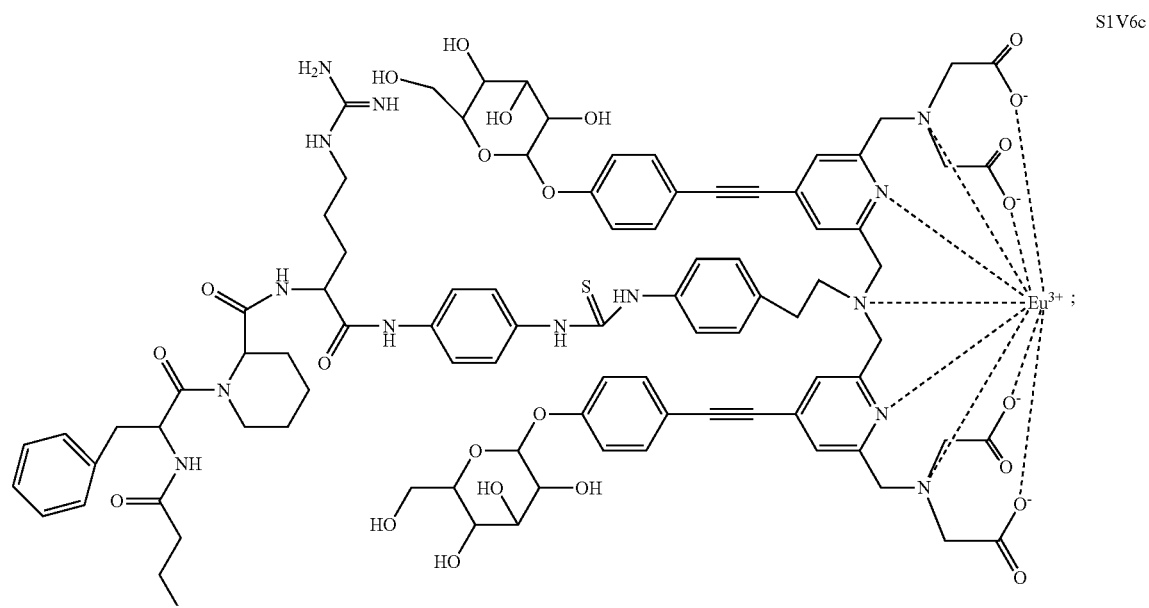

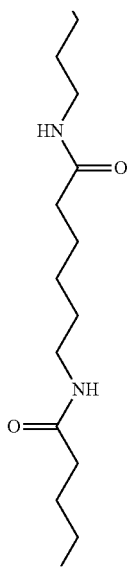
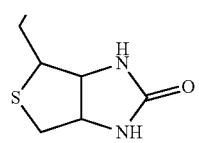
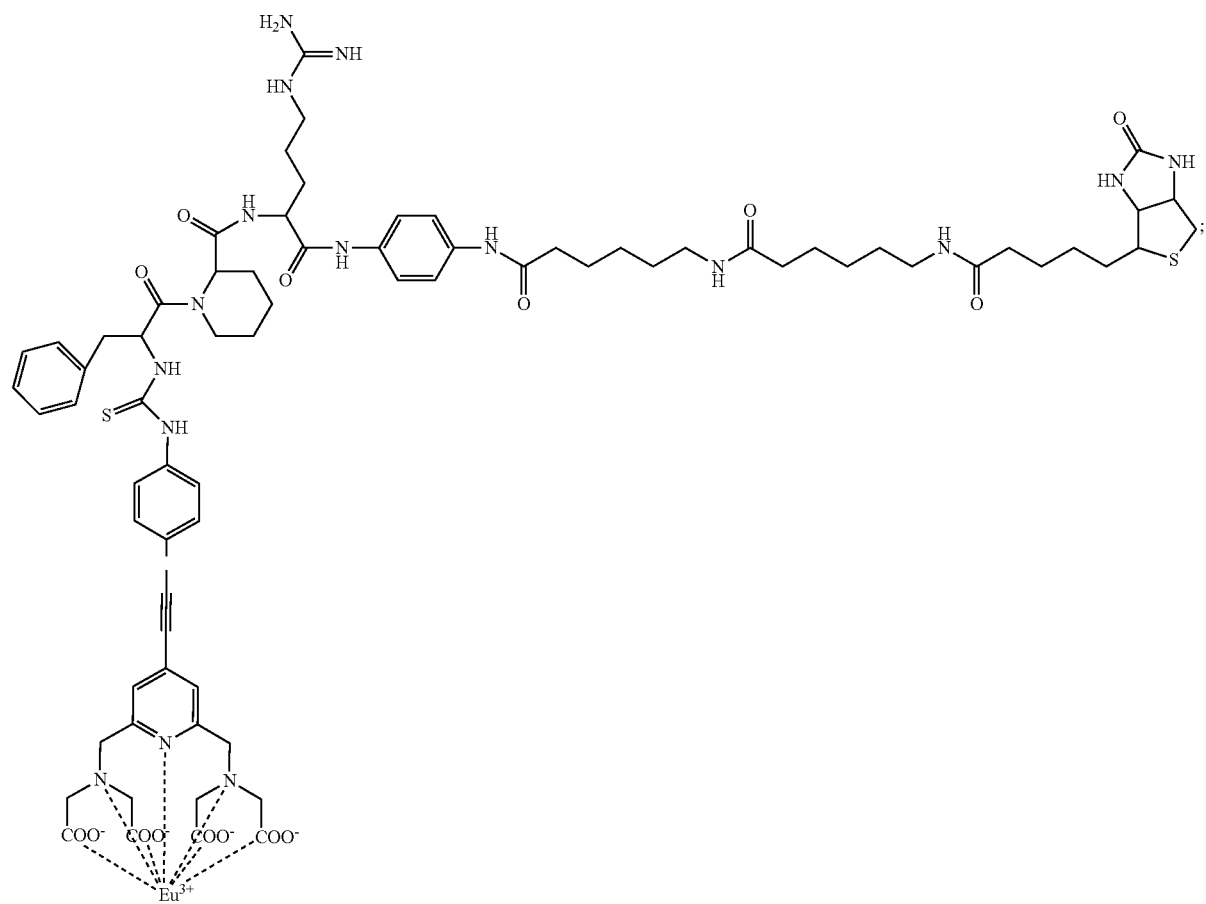
S1V8

-continued
S1V9a
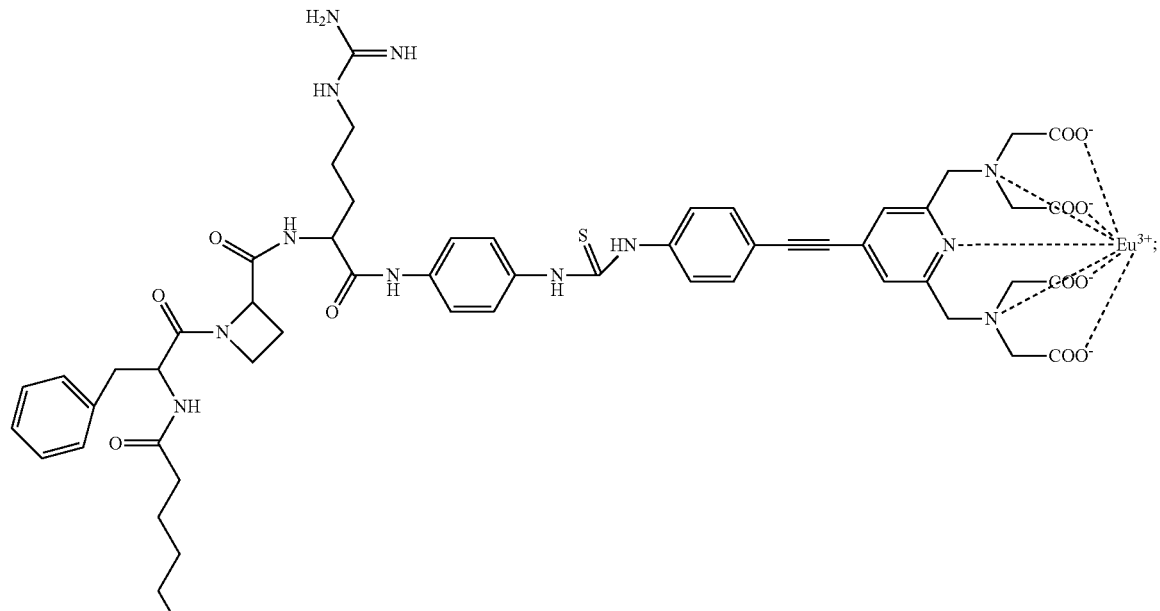
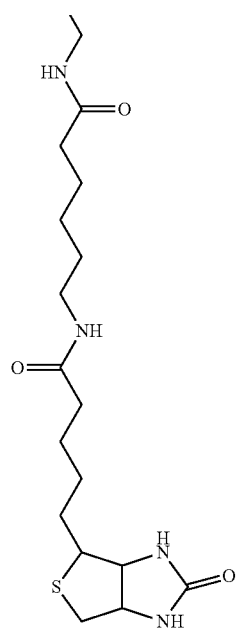

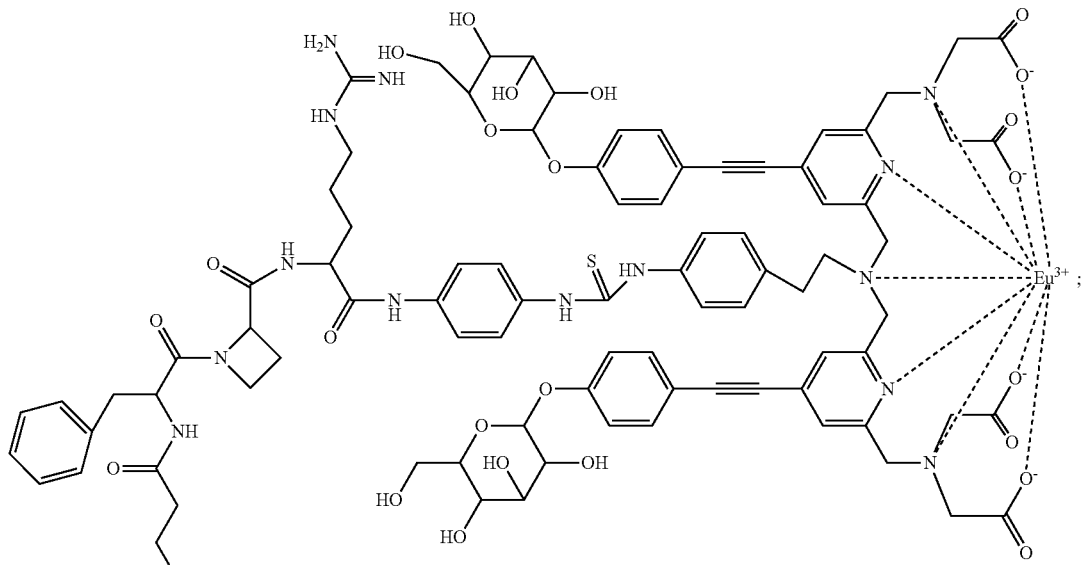
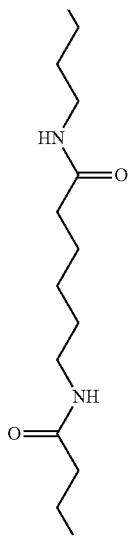
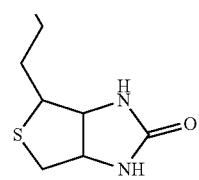

-continued
S1V12a
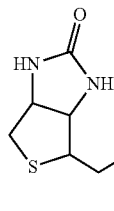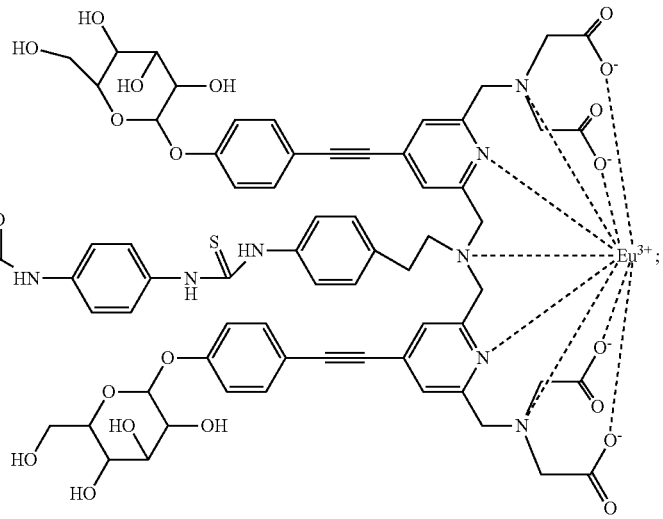
S1V12b
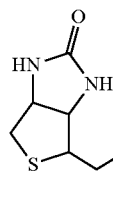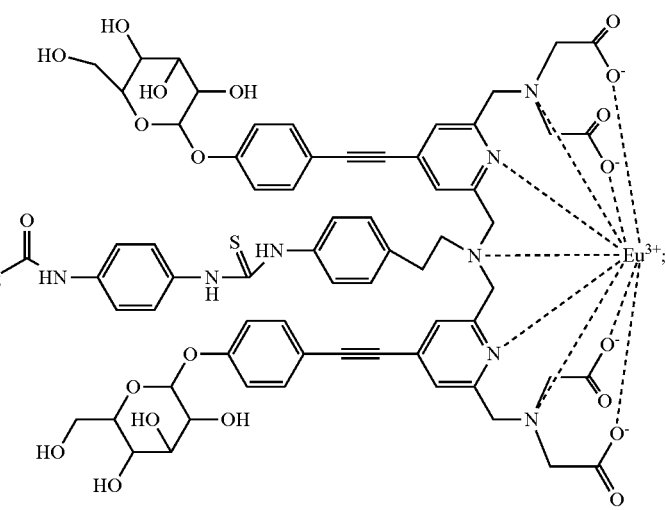
and
S1V12c
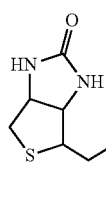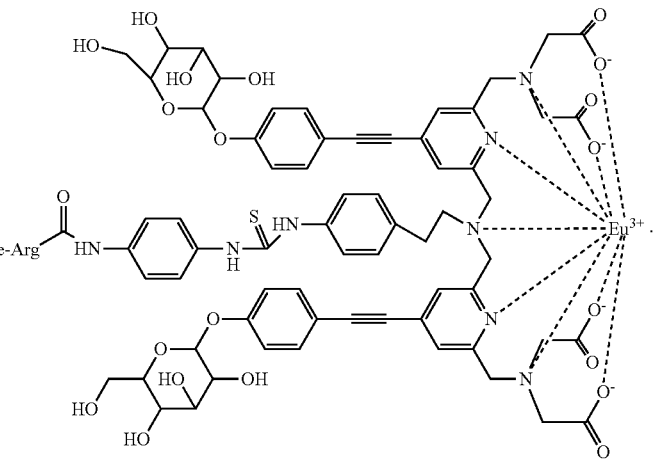

7. A one-step assay method for determining the level of bioactive thrombin in a test sample comprising the steps:
   a) combining, sequentially or simultaneously, a substrate according to claim 1, an activator and said test sample;
   b) incubating the resulting reaction mixture to release thrombin-cleaved, chelate-containing substrate fragments and immobilizing the binding partner-containing substrate fragment and non-thrombin-cleaved intact substrate on an immobilization matrix;
   c) washing off non-immobilized, thrombin-cleaved chelate-containing substrate fragment and non-immobilized, non-thrombin-cleaved substrate, if present;
   d) measuring the level of luminescent emission from immobilized intact substrate; and
   e) calculating thrombin activity from the reduction of intensity of luminescent emission compared to a thrombin-free standard sample,
   wherein said activator is selected from the group consisting of: thromboplastin, partial thromboplastin reagents and contact activators,
   wherein the partial thromboplastin reagents are phospholipids.

8. The assay method according to claim 7, wherein the addition of said sample and activator is performed simultaneously with the addition of the substrate to an immobilization matrix.

9. The assay method according to claim 7, wherein the addition of said sample and activator is performed after immobilization of the substrate on an immobilization matrix.

10. A two-step assay method for determining the level of bioactive thrombin in a test sample comprising the steps:
   a) adding said sample and an activator to a substrate according to claim 1 in liquid phase,
   b) incubating the resulting reaction mixture to release thrombin-cleaved, chelate-containing substrate fragment,
   c) adding the reaction mixture to an immobilization matrix,
   d) washing off non-immobilized, thrombin-cleaved chelate-containing substrate fragment and non-immobilized, non-thrombin-cleaved substrate, if present,
   e) measuring the level of luminescent emission from immobilized intact substrate, and
   f) calculating thrombin activity from the reduction of intensity of luminescent emission compared to a thrombin-free standard sample,
   wherein said activator is selected from the group consisting of thromboplastin, partial thromboplastin reagents and contact activators,
   wherein the partial thromboplastin reagents are phospholipids.

11. The assay method according to claim 10, wherein said contact activators comprise silica, kaolin, celite or ellagic acid.

12. A test kit for determining the level of bioactive thrombin in a sample comprising:
   a) a luminescent substrate according to claim 1, and
   b) a solid immobilization matrix.

13. A substrate for thrombin having the formula:

A-X—Z-A' wherein
one of either A or A' comprises a luminescent chelate, and the other one of A or A' comprises a first partner of a binding pair, optionally including a spacer, and connected via a peptide bond to the remaining part of the substrate;

X forms a tri- or tetra-peptide selected from the group consisting of X'-Phe-Aze-Arg, X'-Phe-Pip-Arg, and X'-Phe-Pro-Arg, wherein X' is absent or is selected from the group consisting of Lys, Ahx, Ile, and Val;

Z is NH—R—Z',
wherein R is selected from the group consisting of $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, $C_{1-6}$alkylenoxy-carbonyl, $C_{1-6}$alkylene-arylene, $C_{1-6}$alkylenoxy-arylene, $C_{1-6}$alkylene-NH, $C_{1-6}$alkylenoxy-NH, $C_{1-6}$alkylene-NHCO, $C_{1-6}$alkylenoxy-NHCO, $C_{1-6}$alkylene-CONH, $C_{1-6}$alkylenoxy-CONH, $C_{1-6}$alkylene-COS, $C_{1-6}$alkylenoxy-COS, $C_{1-6}$alkylene-CONH-$C_{1-6}$alkylene-arylene, arylene, arylene-$C_{1-6}$ alkylene, arylene-$C_{1-6}$alkylenoxy, $(R^1)_a$-arylene-$(NHCO—R^2)_b$, $(R^3)_c$-arylene-$(CONH—R^4)_d$, $(R^5—CONH)_e$-arylene- $(R^6)_f$, and $(R^7—NHCO)_g$-arylene-$(R^8)_h$, wherein each $R^1$, $R^2$, $R^3$, $R^4$, $R^5$, $R^6$, $R^7$, and $R^8$ at each occurrence is independently selected from the group consisting of $C_{1-6}$alkylene, $C_{1-6}$alkylenoxy, $C_{1-6}$thioalkylene, $C_{1-6}$thioalkylenoxy, carbonyl-$C_{1-6}$alkylene, carbonyl-$C_{1-6}$alkylenoxy, $C_{1-6}$alkylene-carbonyl, arylene and arylene-$C_{1-6}$alkylene, and each of a, b, c, d, e, f, g, and h is independently selected from the group consisting of the integers from 0 to 6, wherein the arylene is phenylene, biphenylene or naphthylene, wherein the phenylene, biphenylene or naphthylene is optionally mono-, di- or tri-substituted by one or more substituents selected from the group consisting of halogen, OH, SH, CN, $NO_2$, $C_{1-6}$alkyl, $C_{1-6}$ salkoxy, and $C_{1-6}$alkoxycarbonyl;

Z' is selected from the group consisting of thiourea (—NH—CS—NH—), aminoacetamide (—NH—CO—CH$_2$—NH—), amide (—NH—CO—), methylamide (—NCH$_3$—CO—), substituted-triazine-diamine (—NH—(R$^9$C$_3$N$_3$)—NH—), thioether (—S—), thioacetamide (—S—CH$_2$—CO—NH—), disulfide (—S—S—), (—S—CO—CH$_2$—NH—) (—S—(R$^9$C$_3$N$_3$)—NH—), amide (—CO—NH—, —CO—NCH$_3$—) and ester (—CO—O—), wherein $R^9$ is selected from the group consisting of hydrogen, halogen, $C_{1-6}$alkyl, $C_{1-6}$thioalkyl, $C_{1-6}$alkoxy, $C_{1-6}$thioalkoxy, aryloxy, and amino, which alkyl, thioalkyl, alkoxy, thioalkoxy or aryloxy group is optionally mono-, di- or tri-substituted and which amino group is optionally mono- or di-substituted by one or more substituents selected from the group consisting of halogen, OH, SH, CN, $NO_2$, $C_{1-6}$alkyl, $C_{1-6}$alkoxy, and $C_{1-6}$alkoxycarbonyl, wherein the substrate is selected from the group consisting of:

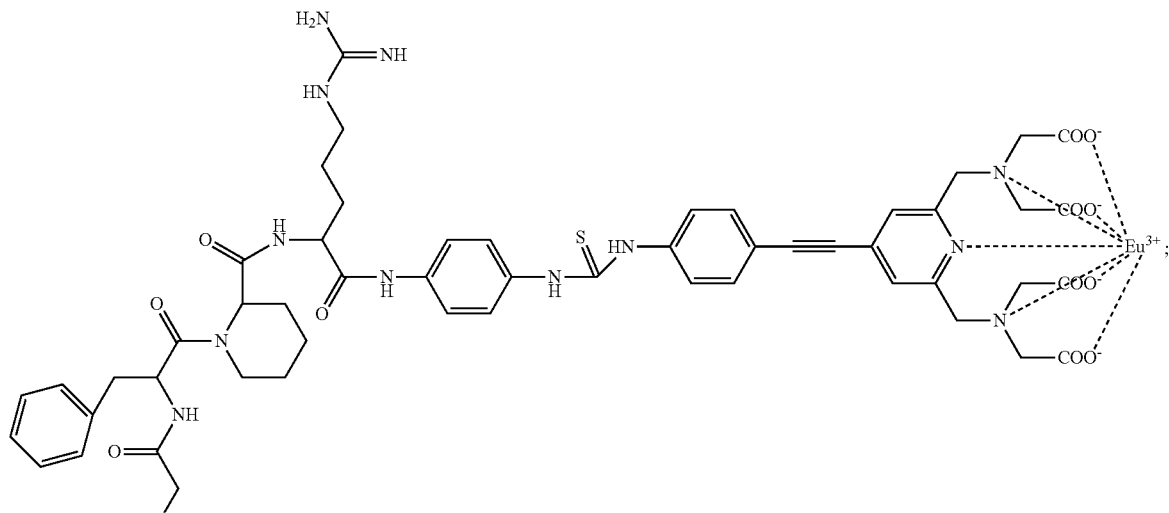
S1V6a
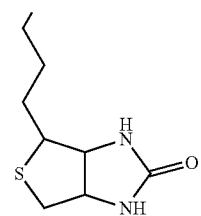
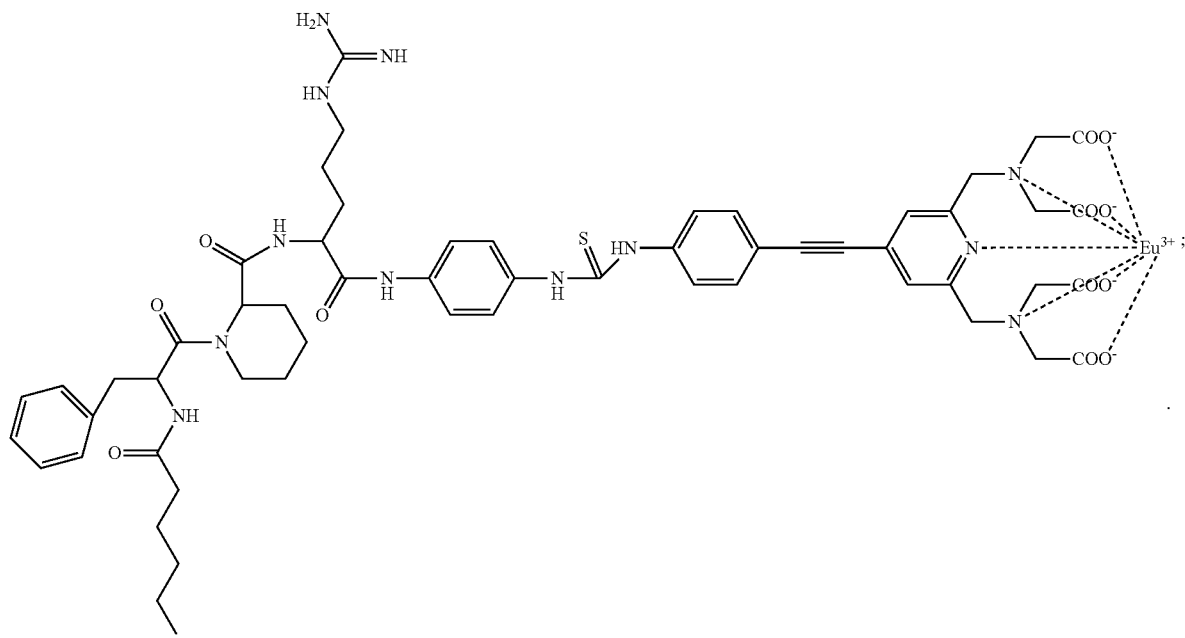
S1V6b

-continued
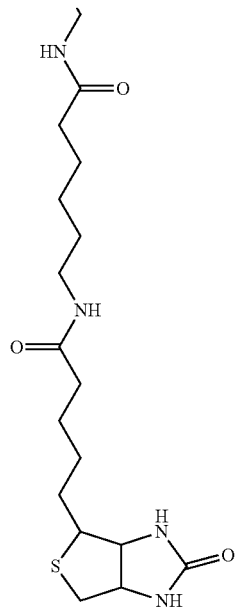
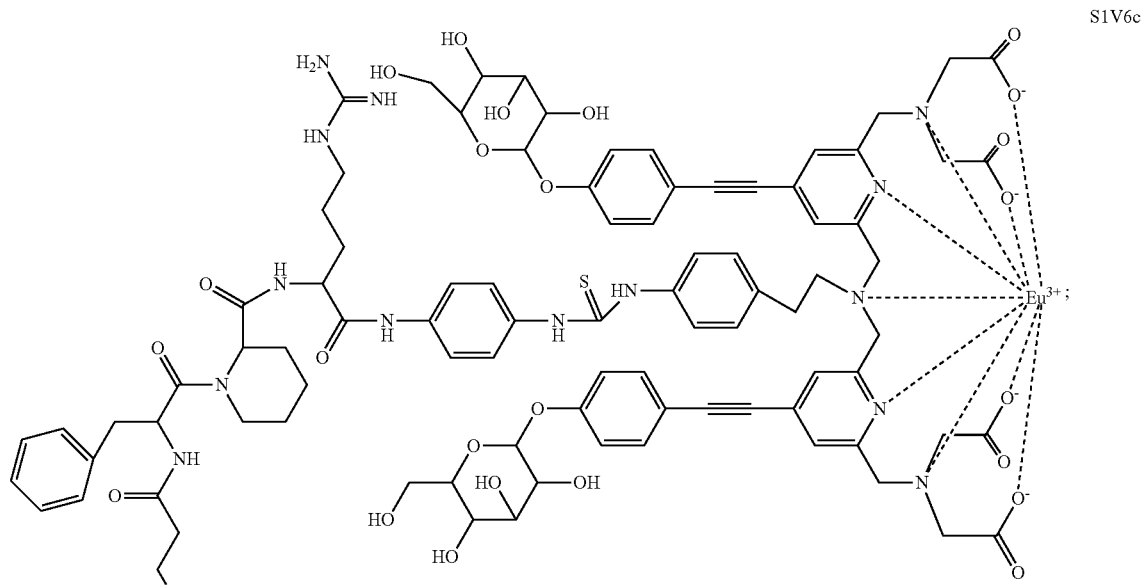
S1V6c

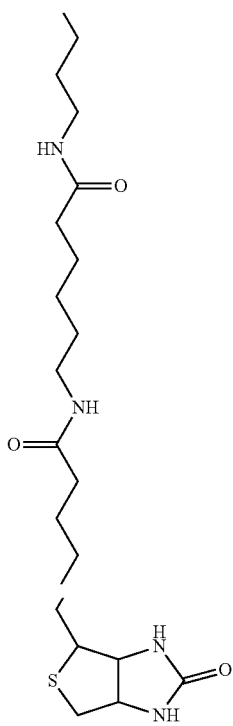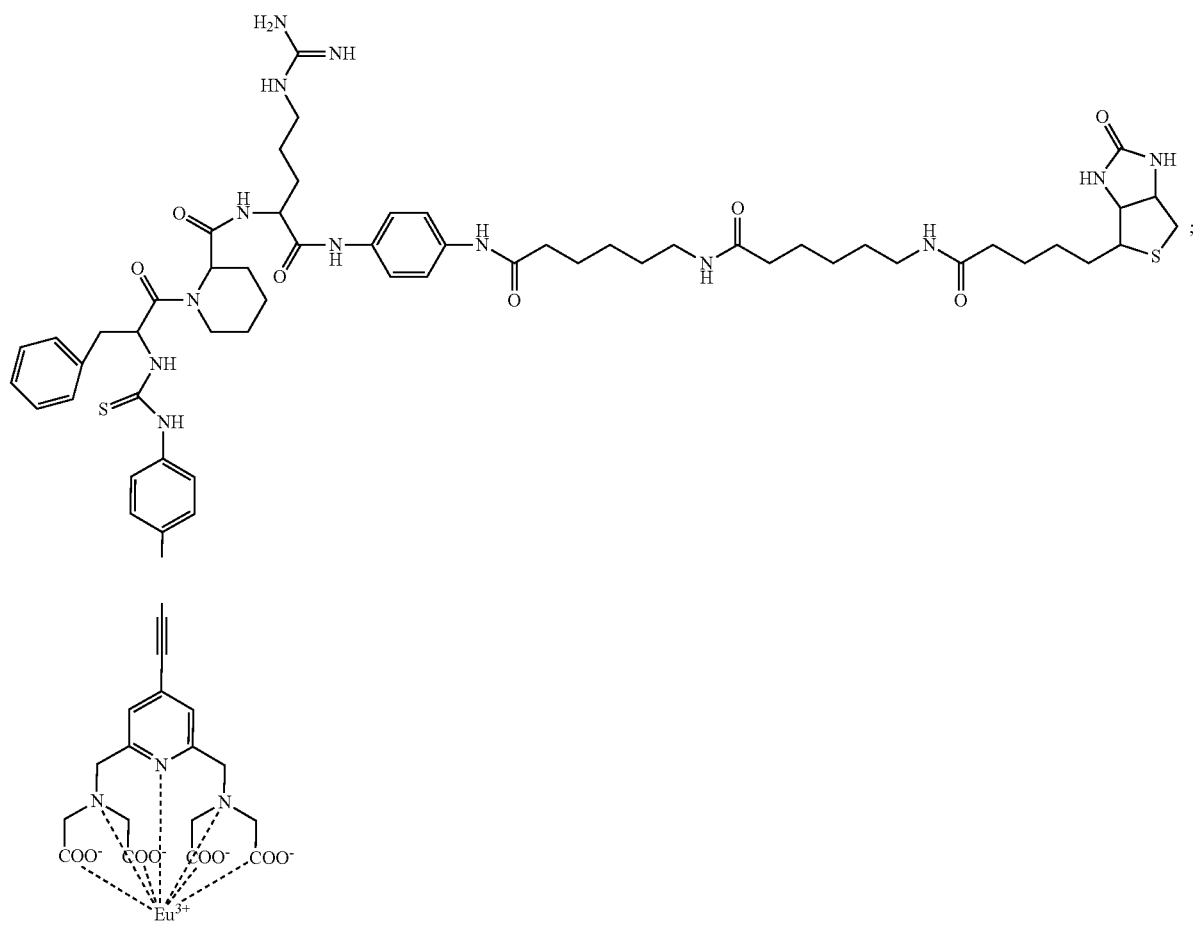
S1V8

S1V9a
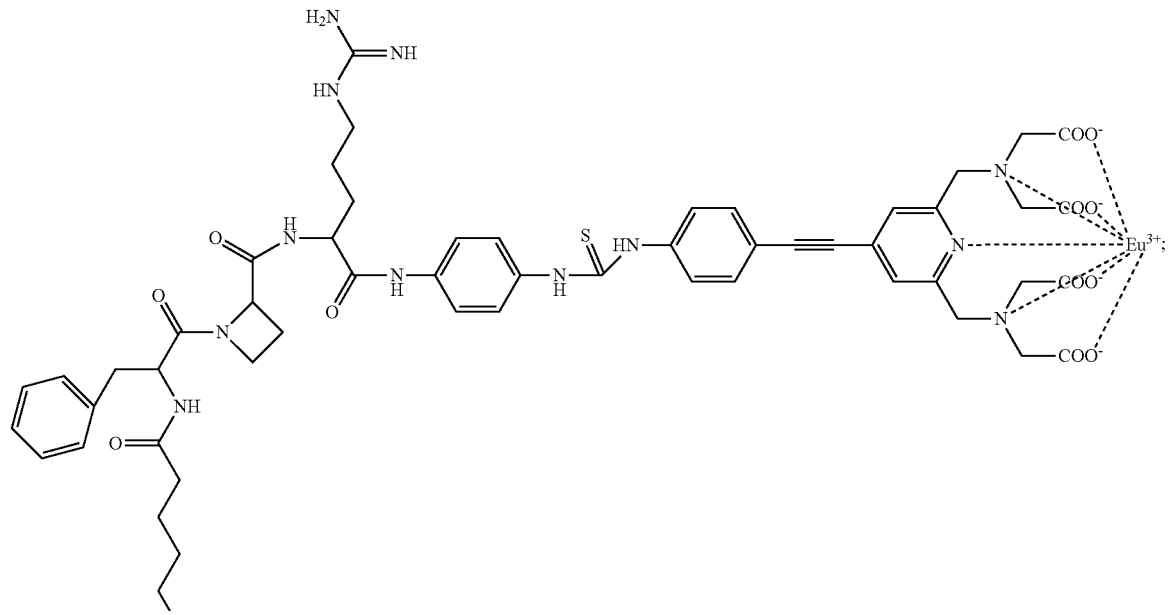
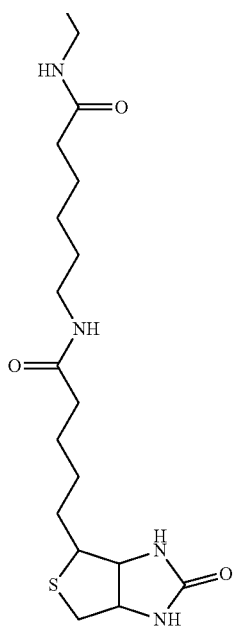

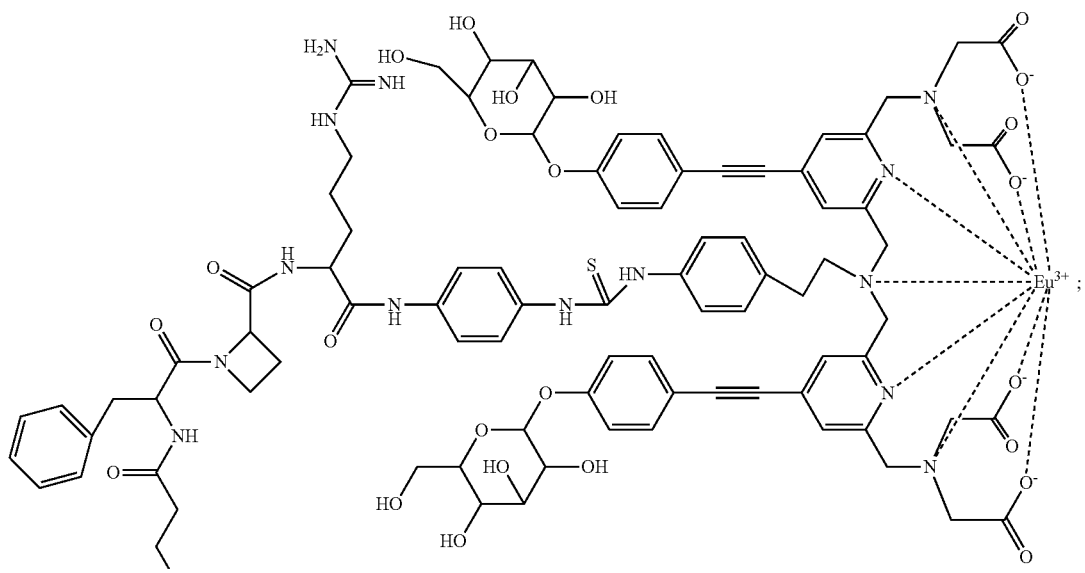
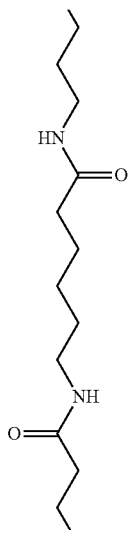
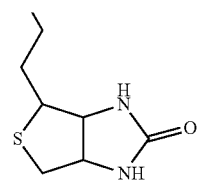

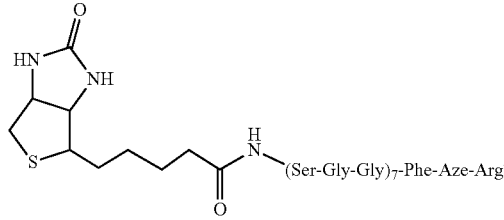
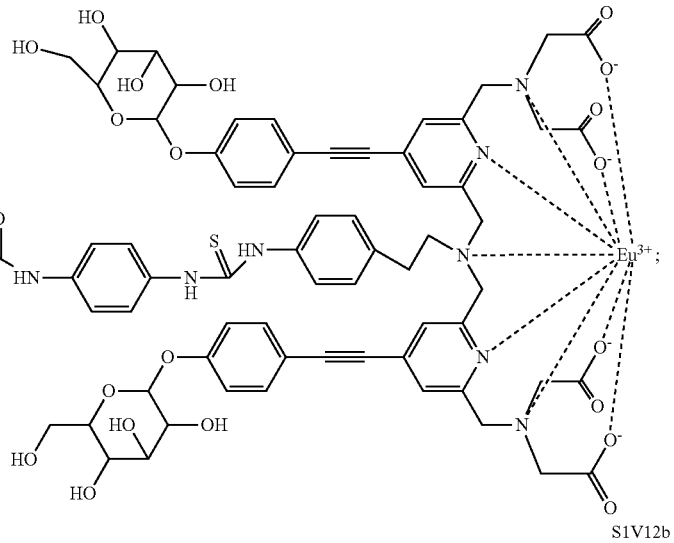
S1V12a
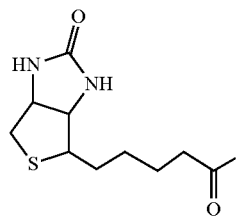
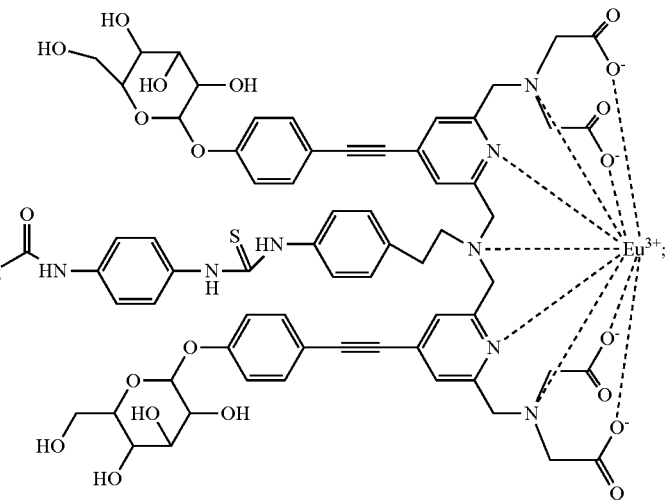
S1V12b
and
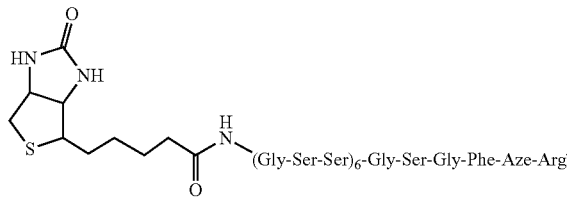
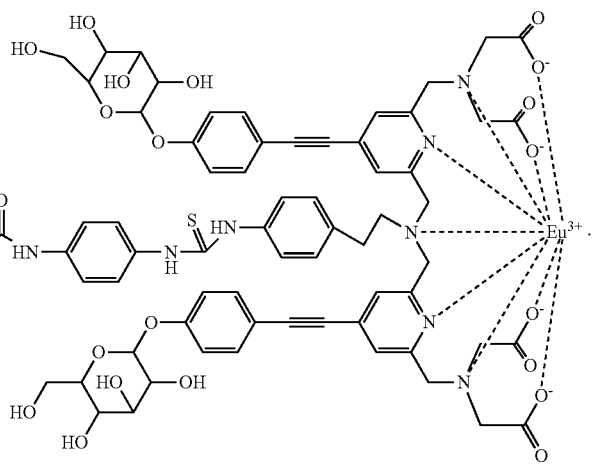
S1V12c
* * * * *

UNITED STATES PATENT AND TRADEMARK OFFICE
CERTIFICATE OF CORRECTION

PATENT NO. : 8,535,898 B2  
APPLICATION NO. : 12/503602  
DATED : September 17, 2013  
INVENTOR(S) : Qui-Ping Qin et al.

Page 1 of 6

It is certified that error appears in the above-identified patent and that said Letters Patent is hereby corrected as shown below:

The molecule figure labeled "S1V6a" appearing at columns 7-9 of the specification, claim 6, columns 27-28, and claim 13, columns 41-42, should be replaced to correct breaks in the molecule's bond linkage. The figures should appear as:

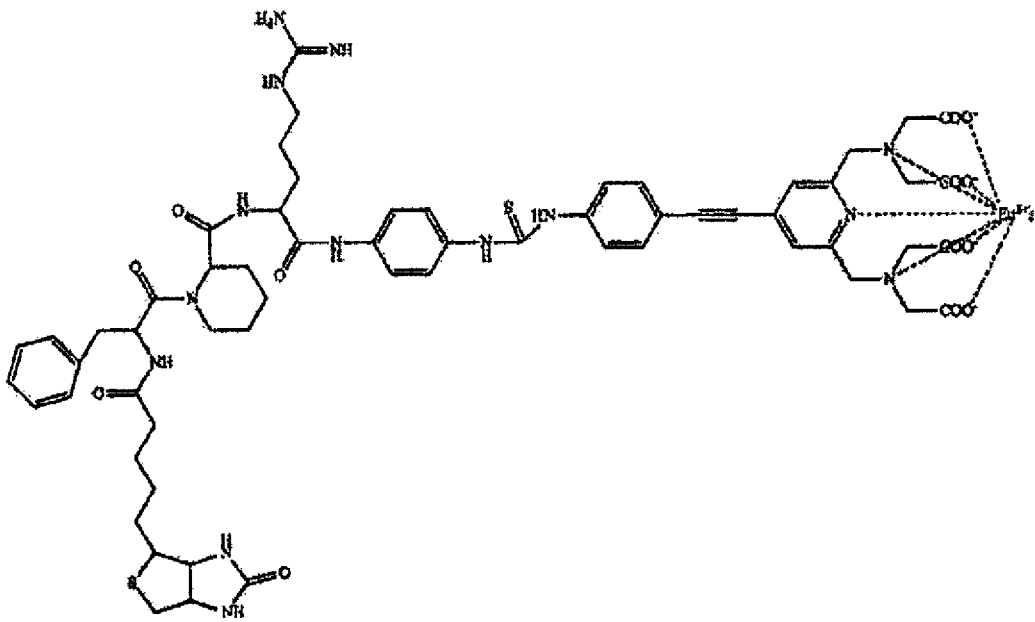

Signed and Sealed this  
Twenty-sixth Day of August, 2014

Michelle K. Lee  
*Deputy Director of the United States Patent and Trademark Office*

CERTIFICATE OF CORRECTION (continued)
U.S. Pat. No. 8,535,898 B2

The molecule figure labeled "S1V6b" appearing at columns 9-10 of the specification, claim 6, columns 27-29, and claim 13, columns 41-43, should be replaced to correct breaks in the molecule's bond linkage. The figures should appear as:

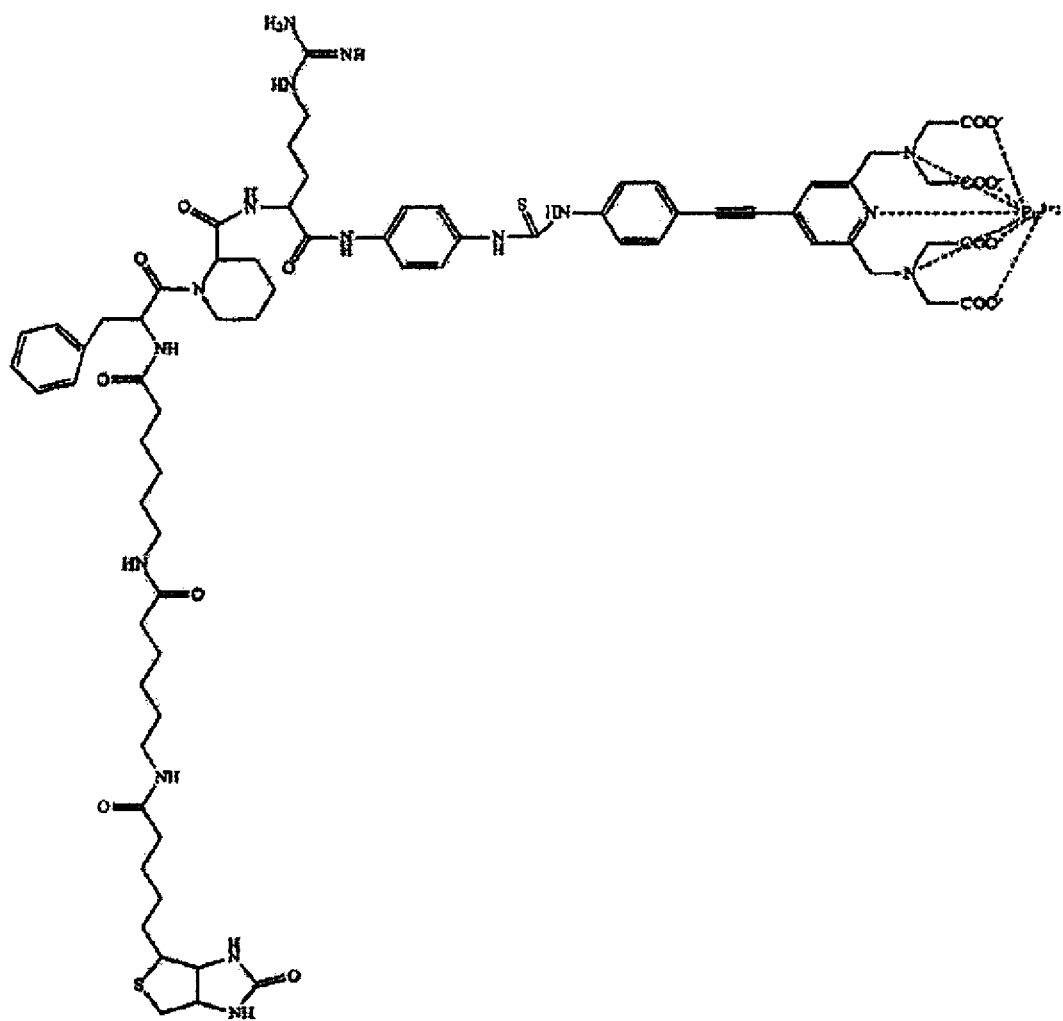

CERTIFICATE OF CORRECTION (continued)
U.S. Pat. No. 8,535,898 B2

Page 3 of 6

The molecule figure labeled "S1V6c" appearing at columns 11-12 of the specification, claim 6, columns 29-31, and claim 13, columns 43-45, should be replaced to correct breaks in the molecule's bond linkage. The figures should appear as:

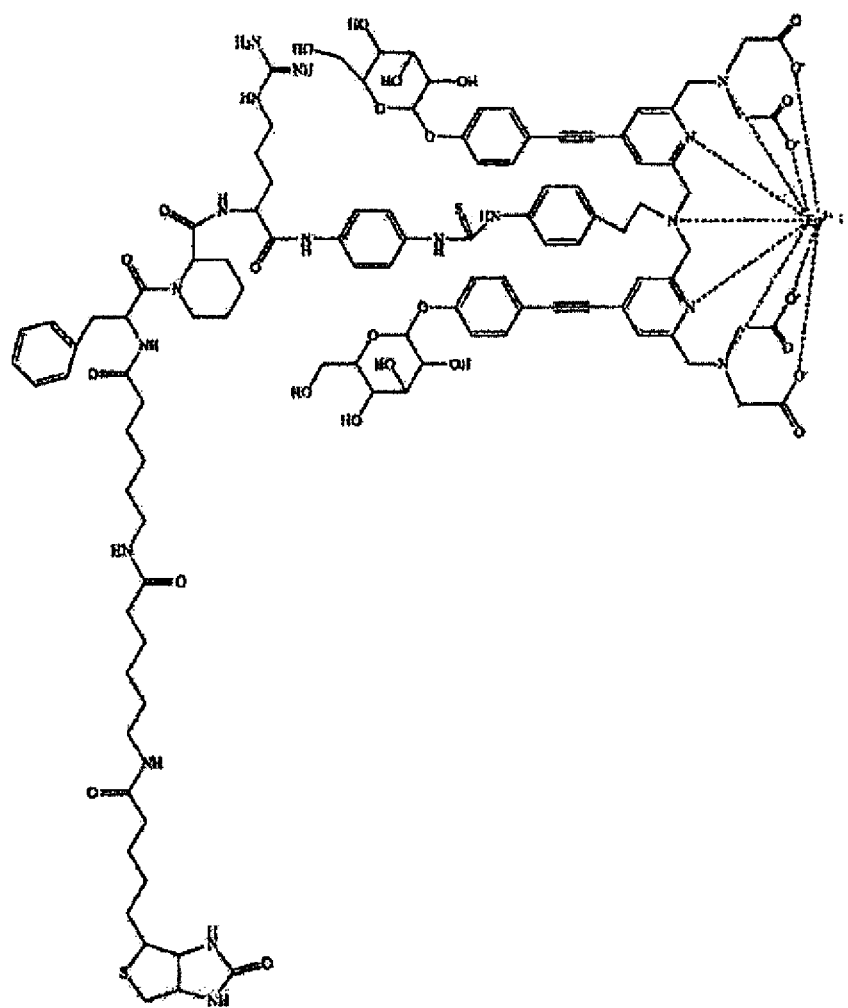

CERTIFICATE OF CORRECTION (continued)
U.S. Pat. No. 8,535,898 B2

Page 4 of 6

The molecule figure labeled "S1V8" appearing at columns 13-14 of the specification, claim 6, columns 31-32, and claim 13, columns 45-46, should be replaced to correct breaks in the molecule's bond linkage. The figures should appear as:

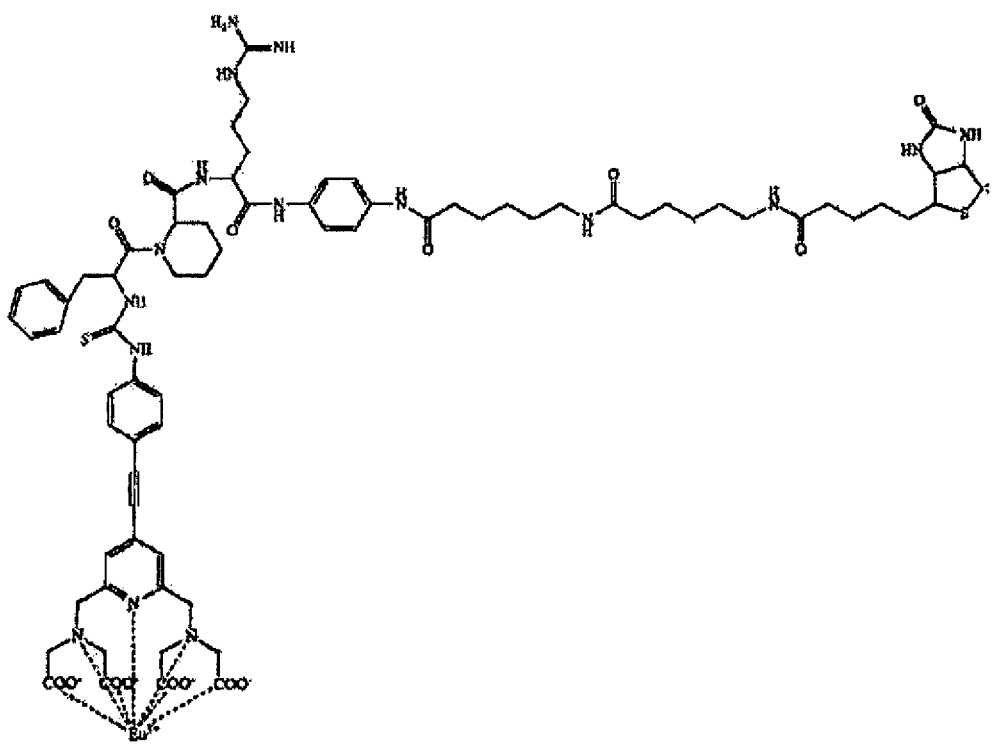

CERTIFICATE OF CORRECTION (continued)
U.S. Pat. No. 8,535,898 B2

Page 5 of 6

The molecule figure labeled "S1V9a" appearing at columns 13-15 of the specification, claim 6, columns 33-34, and claim 13, columns 47-48, should be replaced to correct breaks in the molecule's bond linkage. The figures should appear as:

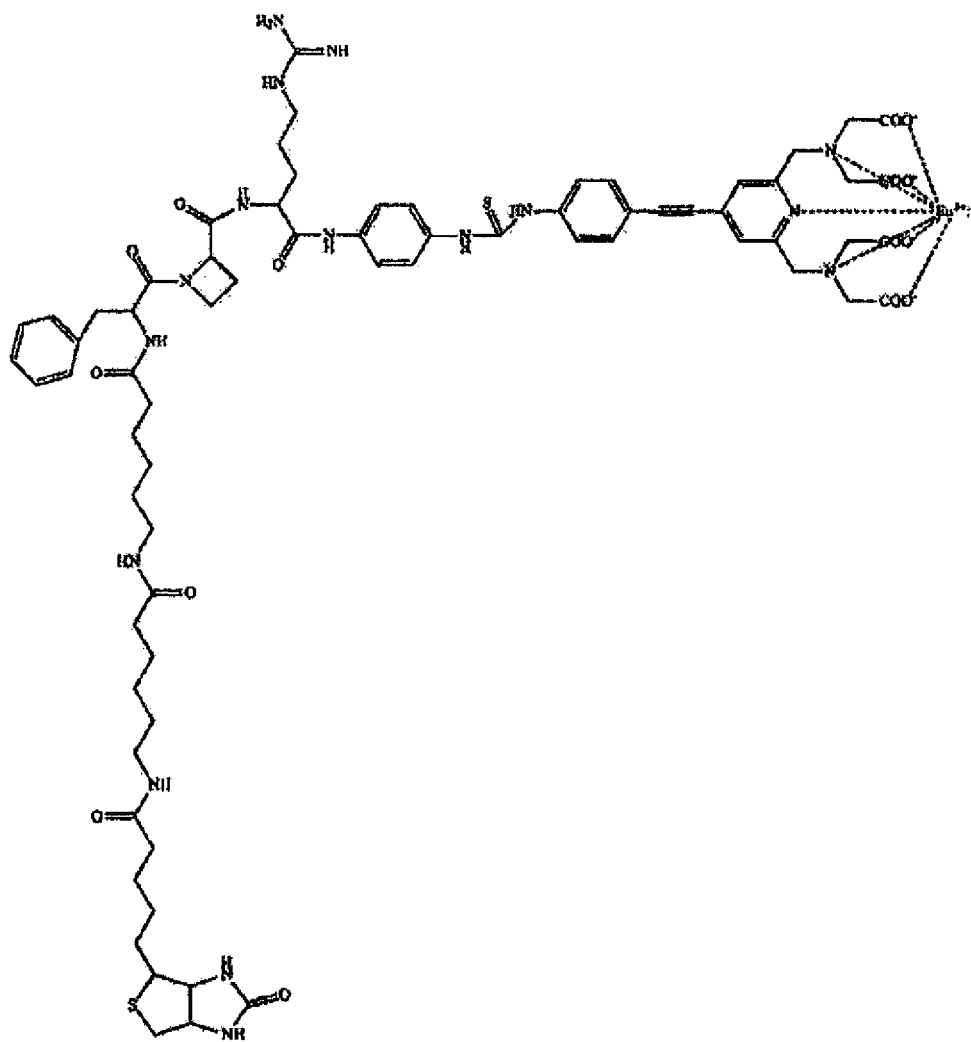

CERTIFICATE OF CORRECTION (continued)
U.S. Pat. No. 8,535,898 B2

The molecule figure labeled "S1V9b" appearing at columns 15-17 of the specification, claim 6, columns 35-36, and claim 13, columns 49-50, should be replaced to correct breaks in the molecule's bond linkage. The figures should appear as: